United States Patent
Greenwald et al.

(10) Patent No.: US 6,624,142 B2
(45) Date of Patent: Sep. 23, 2003

(54) TRIMETHYL LOCK BASED TETRAPARTATE PRODRUGS

(75) Inventors: Richard B. Greenwald, Somerset, NJ (US); Hong Zhao, Edison, NJ (US)

(73) Assignee: Enzon, Inc., Bridgewater, NJ (US)

( * ) Notice: Subject to any disclaimer, the term of this patent is extended or adjusted under 35 U.S.C. 154(b) by 199 days.

(21) Appl. No.: 09/852,335

(22) Filed: May 9, 2001

(65) Prior Publication Data

US 2002/0006898 A1 Jan. 17, 2002

Related U.S. Application Data

(63) Continuation-in-part of application No. 09/137,430, filed on Aug. 21, 1998, now Pat. No. 6,303,569, which is a continuation-in-part of application No. 09/000,676, filed on Dec. 30, 1997, now Pat. No. 5,965,119.

(51) Int. Cl.[7] .................. A61K 31/222; A61K 31/704; A61K 31/7068; A61K 38/06; A61K 38/07
(52) U.S. Cl. ........................... 514/2; 424/1.11; 514/18; 514/34; 514/49; 514/345; 514/424; 514/546; 514/551; 530/330; 530/331; 530/345; 530/408; 530/409; 530/410; 536/6.4; 536/28.5; 546/290; 546/300; 546/301; 548/556; 560/129; 560/155; 560/170
(58) Field of Search .................. 424/1.11, 9.1, 424/85.1, 94.3; 514/2, 15, 16, 17, 18, 19, 34, 49, 241, 247, 269, 291, 296, 345, 372, 380, 404, 422, 423, 424, 445, 473, 480, 490, 529, 546, 551, 564, 646, 656; 530/328, 329, 330, 331, 345, 408, 409, 410; 435/188; 525/50, 54.1, 403; 534/10; 536/6.4, 28.5; 544/180, 239, 298; 546/82, 110, 279.1, 290, 300, 301; 548/213, 243, 364.1, 370.1, 370.4, 518, 556; 549/66, 479; 560/129.155, 157, 170; 562/449

(56) References Cited

U.S. PATENT DOCUMENTS

| | | | |
|---|---|---|---|
| 4,179,337 A | 12/1979 | Davis et al. | 435/181 |
| 5,093,531 A | 3/1992 | Sano et al. | 568/337 |
| 5,112,739 A | 5/1992 | Meneghini et al. | 436/546 |
| 5,122,614 A | 6/1992 | Zalipsky | 548/520 |
| 5,130,126 A | 7/1992 | Koyama et al. | 424/78.18 |
| 5,321,095 A | 6/1994 | Greenwald | 525/404 |
| 5,349,001 A | 9/1994 | Greenwald et al. | 525/408 |
| 5,561,119 A | 10/1996 | Jacquesy et al. | 514/34 |
| 5,605,976 A | 2/1997 | Martinez et al. | 525/408 |
| 5,643,575 A | 7/1997 | Martinez et al. | 424/194.1 |
| 5,672,584 A | 9/1997 | Borchardt et al. | 514/11 |
| 5,710,135 A | 1/1998 | Leenders et al. | 514/34 |
| 5,965,119 A | 10/1999 | Greenwald et al. | 424/78.37 |
| 6,303,569 B1 * | 10/2001 | Greenwald et al. | 514/2 |

FOREIGN PATENT DOCUMENTS

| | | |
|---|---|---|
| WO | WO 98/13059 | 4/1998 |
| WO | 99/30727 * | 6/1999 |

OTHER PUBLICATIONS

The Merck Index, 13th edition. O'Neil et al, eds. Whitehouse Station: Merck & Co., Inc. 2001, p. 1041.*

Greenwald, Richard B., et al., *Drug Delivery Systems Based on Trimethyl Lock Lactonization: Poly(ethylene glycol) Prodrugs of Amino–Containing Compounds*, Journal of Medical Chemistry, vol. 43, No. 3, pp. 475–487 (2000).

de Bont, Dries B.A., et al.,*Synthesis and Biological Activity of B–Glucuronyl Carbamate–Based Prodrugs of Paclitaxel as Potential Candidates for ADEPT*, Bioorganic & Medicinal Chemistry, vol. 5, No. 2, pp. 405–414 (1997).

Shearwater Polymers, Inc., *Catalog–Polyethylene Glycol Derivatives, 1997–1998*; p. 8,33.

Leenders, R.G.G.et al., *Highly Diastereoselective Synthesis of Anomeric B–O–Glycopyranosyl Carbamates from Isocyanates*, Synthesis Nov. 1996; pp 1309–1312.

Leenders, R.G.G. et al, *B–Glucuronyl Carbamate Based Pro–moieties Designed for Prodrugs in ADEPT*, 1995; Tetrahedron Letters vol. 36, No. 10 pp. 1701–1704.

Waldmann, H. et al, *Synthesis of the Palmitoylated and Farnesylated C–Terminal Lipohexapeptide of the Human N–Ras Protein by Employing. . .* , Angew. Chem Int. Ed. 1995, 34 No.20 ; pp. 2259–2262.

Jungheim, L.N. et al., *Design of Antitumor Prodrugs: Substrates for Antibody Targeted Enzymes*, Chem. Rev. 1994; 94 pp. 1553–1566.

Bundgaard, H. *The Double Prodrug Concept and its Applications*, Advanced Drug Delivery Reviews, 3 1989 pp. 39–65.

Wakselman, M. et al., *An Alkali–labile Substituted Benzyloxycarbonyl Amino–protecting Group*, JCS Chem. Comm1973; pp. 593–594.

Carl, P.L. et al. *A Novel Connector Linkage Applicable in Prodrug Design*, J. Med.Chem (1981) vol.24, No. 5 479–480.

Wang, B. et al. *Synthesis of a Novel Esterase–Sensitive Cuclic Prodrug System for Peptides That Utilizes Utilizes a "Trimethyl Lock" Facilitated Lactonization Reaction* J. Org.Chem (1997), 62, 1363–67.

Amsberry, K.L. et al. *The Lactonization of 2'–Hydroxyhydrocinnamic Acid Amides: A Potential Pro for Amines*, J.Org.Chem (1990) 55 5867–5877.

Carpino, L.A., *Reductive Lactoinization of Strategically Methylated Quinone Propionic Acid Ester Amides*, J.Org.Chem (1989) 54 53303–3310.

Wang, B. et al. *Chemical Feasibility Studies of a Potential Coumarin–BAsed Prodrug System*, Bioorganic & Medicinal Chemistry Letters, vol.6, No.8, pp945–950, (1996).

Wang et al *Coumarin–based Prodrugs 2. Synthesis and Biorevesibility Studies of an Esterase–Sensitive Cyclic Prodrug of DADLE* . . .Bioorg. & Med. Chem.Lett vol.6, No23 2823–26 (1996).

Amsberry, K et al. *Amine Prodrugs Which Hydrolyze Amide Lactonization. I. A potential Redox–Sensitive Amide Prodrug*, Pharmaceutical Research vol.8, No.3, 1991, pp. 455–461.

Shan, D., et al., Prodrug Strategies Based on Intramolecular Cyclization Reactions, Journal of Pharmaceutical Sciences, Jul. 1997, vol. 86, No. 7, pp 765–767.

Hermentin et al. Attachment of Rhodosaminylanthracyclinone . . . Bioconj. Chem. 1990. vol. 1, No. 2, pp. 100–107.

\* cited by examiner

*Primary Examiner*—Jeffrey E. Russel
(74) *Attorney, Agent, or Firm*—Muserlian, Lucas & Mercanti, LLP

(57) ABSTRACT

The invention is directed primarily to compounds of Formula I:

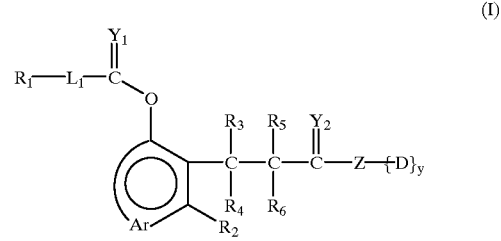

wherein:

$R_1$ is a polymeric residue;

$L_1$ is a bifunctional linking group;

$Y_1$ and $Y_2$ are independently O, S or $NR_7$;

$R_{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

D is a moiety that is a leaving group or a residue of a compound to be delivered into a cell;

Z is selected from the group consisting of:
a moiety that is actively transported into a target cell, a hydrophobic moiety, and combinations thereof;

Ar is a moiety which when included in Formula (I) forms a multi-substituted aromatic hydrocarbon or a multi-substituted heterocyclic group; and (y) is a positive integer greater than or equal to 1.

Methods of making and using the same are also disclosed.

27 Claims, 6 Drawing Sheets

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: Peptide linker -continued

<400> SEQUENCE: 1

Gly Phe Leu Gly
1

TRIMETHYL LOCK BASED TETRAPARTATE PRODRUGS

CROSS REFERENCE TO RELATED APPLICATIONS

This application is a continuation-in-part of U.S. patent application Ser. No. 09/137,430, filed on Aug. 21, 1998, now U.S. Pat. No. 6,303,569, which in turn is a continuation-in-part of U.S. patent application Ser. No. 09/000,676, filed on Dec. 30, 1997, now U.S. Pat. No. 5,965,119, the contents of both of which are incorporated herein by reference.

TECHNICAL FIELD

The present invention relates to tetrapartate prodrugs. In particular, the invention relates to multi-part polymer conjugates that deliver active agents e.g., antitumor agents or the like, linked to cellular uptake enhancing moieties.

BACKGROUND OF THE INVENTION

Over the years, several methods of administering biologically-effective materials to mammals have been proposed. Many biologically-effective materials, e.g., including medicinal agents and the like, are available as water-soluble salts and can be included in pharmaceutical formulations relatively easily. Problems arise when the desired biologically-effective material is either insoluble in aqueous fluids or is rapidly degraded in vivo. For example, alkaloids are often especially difficult to solubilize.

One way to solubilize biologically-effective material(s) is to include them as part of a soluble prodrug. Thus, prodrugs include chemical derivatives of a biologically-active material, or parent compound which, upon administration, eventually liberate the parent compound in vivo. Prodrugs allow the artisan to modify the onset and/or duration of action of an agent in vivo and can modify the transportation, distribution or solubility of a drug in the body. Furthermore, prodrug formulations often reduce the toxicity and/or otherwise overcome difficulties encountered when administering pharmaceutical preparations.

Typical examples of prodrugs include organic phosphates or esters of alcohols or thioalcohols. See *Remington's Pharmaceutical Sciences,* 16th Ed., A. Osol, Ed. (1980), the disclosure of which is incorporated by reference herein.

Prodrugs are, by definition, largely inactive forms of the parent or active compound. The rate of release of the active drug, typically, but not exclusively, by hydrolysis of the prodrug, is influenced by several factors, but especially by the type of bond joining the active drug to the modifier. Care must be taken to avoid preparing prodrugs which are eliminated through the kidney or reticular endothelial system, etc., before a sufficient amount of the parent compound is released. By incorporating a polymer as part of the prodrug system, one can increase the circulating half-life of the drug. However, in some situations, such as with alkaloids, it has been determined that when only one or two polymers of less than about 10,000 daltons are conjugated thereto, the resulting conjugates are rapidly eliminated in vivo especially if a somewhat hydrolysis-resistant linkage is used. In fact, such conjugates are so rapidly cleared from the body that even if a hydrolysis-prone ester linkage is used, not enough of the parent molecule is regenerated in vivo. This is often not a concern with moieties such as proteins, enzymes and the like, even when hydrolysis-resistant linkages are often used. In those cases multiple polymer strands, each having a molecular weight of about 2–5 kDa, are used to further increase the molecular weight and circulating half-life.

Some ways in which these problems have been addressed are described, for example, in the above-mentioned patents, e.g. U.S. Pat. No. 6,303,569 and U.S. Pat. No. 5,965,119. These teach double prodrugs, i.e., tripartate, that comprise polymer conjugates of various biologically-effective materials, and methods of making these conjugates. The double prodrug linkages are selected to hydrolyze in vivo at a rate which generates sufficient amounts of the "second" and more reactive prodrug compound within a suitable time after administration by, a trimethyl lock elimination reaction, providing improved control of the pharmacokinetics of a number of small molecule drugs, agents and the like. However, further opportunities for particularly selective targeting of diagnostic and/or therapeutic agents to tissues or cells of interest, by means of a rationally designed prodrug conjugate remain.

One particularly desirable target tissue for prodrugs is tumor tissue. It is well known that tumors generally exhibit abnormal vascular permeability characterized by enhanced permeability and retention ("EPR effect"). This EPR effect advantageously allows biologically-effective materials, in the form of macromolecules, e.g., protein(s) such as enzymes and/or antibodies and derivatives or fragments thereof, or the like, to readily enter tumor interstitial tissue space (see, for example, the review article by Maeda et al., 2000, *J. of Controlled Release,* 65:271–284, incorporated by reference herein). Certain other tissues, in addition to tumors, can exhibit this same EPR effect, under conditions of inflammation, and the like.

In brief, and without being bound by any theory or hypothesis as to the working of the EPR effect, it is believed that the EPR effect allows penetration of large molecule or macromolecule substances, including polymer-based delivery systems. This provides a substantially selective delivery of polymer conjugates into tumor tissue space, e.g., tumor interstitial space. Thereafter, however, the same EPR effect is believed to allow the released prodrug(s) and/or any newly released relatively low molecular weight, biologically-effective materials, to rapidly diffuse out of the extracellular tissue space of the targeted tissue. It is believed that if the released active agent fails to be taken up by the surrounding cells at a sufficient rate, they diffuse away from the release site in the ongoing blood or lymphatic flow.

Thus, there continues to be a need to provide additional technologies for forming prodrugs which would benefit from the multiple level prodrug concept and compensate or control for the EPR effect by allowing for more rapid update or transport of the released biologically-effective materials into tumor cells and/or cells of other tissues of interest that exhibit the EPR effect.

SUMMARY OF THE INVENTION

In one aspect of the invention, compounds of Formula (I) are provided:

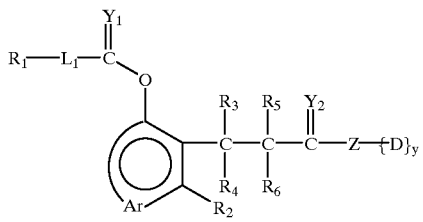

(I)

wherein:

$R_1$ is a mono- or bivalent polymer residue, e.g., having a number average molecular weight of from about 2,000 to about 100,000 Daltons.

$L_1$ is a bifunctional linking group;

$Y_1$ and $Y_2$ are independently O, S or $NR_7$;

$R_{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is a moiety which when included in Formula (I) forms a multi-substituted aromatic hydrocarbon or a multi-substituted heterocyclic group;

D is a residue of a compound to be delivered into a cell or a leaving group;

(y) is a positive integer greater than or equal to 1; and

Z is covalently linked to $[D]_y$ and selected from a moiety that is actively transported into a target cell, a hydrophobic moiety or a combination thereof.

Methods of preparing and using the inventive tetrapartate prodrugs are also provided. The methods of use include methods of treating a disease or disorder in an animal and include administering a pharmaceutically acceptable composition comprising an effective amount of a compound of Formula I, to an animal in need thereof. One particular method includes delivering a biologically active material, designated D herein, into a cell in need of treatment therewith. The method involves administering a compound of Formula I to an animal containing the cell in need of treatment and wherein the compound of Formula I is hydrolyzed in vivo extracellularly to yield:

Formula I-(i)

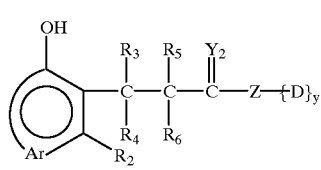

after hydrolysis of the polymeric residue ($R_1$ and linker); and Formula (I-i) subsequently spontaneously hydrolyzes to Formula (I-ii)

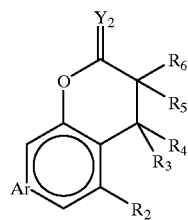

and Formula I-(iii) Z—[D]y;

Z—[D]y then crosses the membrane of the cell, and is hydrolyzed therein to release D.

DETAILED DESCRIPTION OF THE INVENTION

A. Overview

Figure 1:
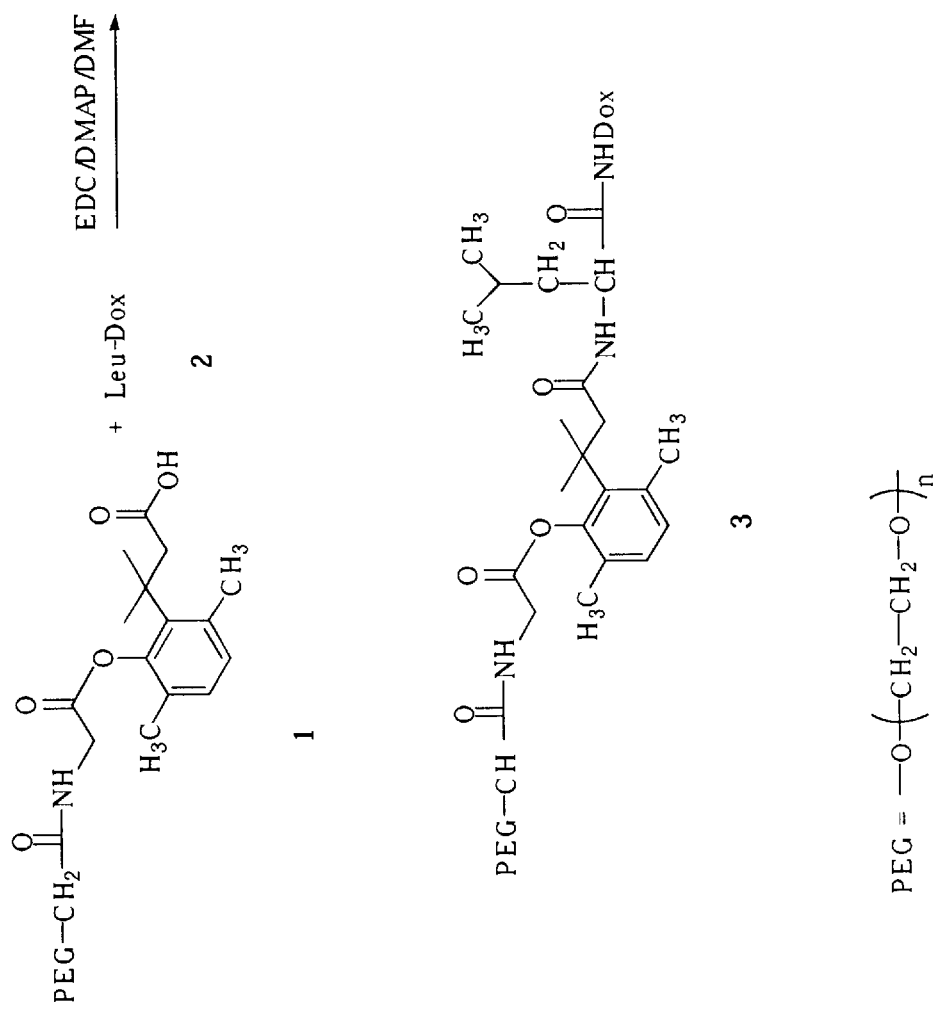
FIGS. 1–2 schematically illustrate methods of forming compounds of the present invention.

The invention provides triple prodrugs compositions, hereinafter, "tetrapartate" prodrugs for delivering a biologically active material into certain target cells, such as, for instance, tumor cells, as well as methods of making and using the same. The tetrapartate prodrug compositions of the present invention contain separate hydrolyzable or cleavable linkages between the polymer portion, the trimethyl lock portion, enhancer and biologically active materials. The biologically active material is, for example, a moiety derived from a biologically active nucleophile, i.e., a native or unmodified drug or diagnostic tag. These linkages are preferably ester and/or amide linkages designed to hydrolyze at a rate which generates sufficient amounts of the biologically active parent compound in a suitable time after the polymer transport portion has been released. The term "sufficient amounts" for purposes of the present invention shall mean an amount which achieves a therapeutic effect.

The present invention is broadly based upon the principle that biologically active materials suitable for incorporation into the polymer-based prodrug conjugates, e.g., the double prodrug compositions as discussed supra, may themselves be substances/compounds which are not active after hydrolytic release from the linked composition, but which will become active after undergoing a further chemical process/reaction, thus providing triple-acting prodrugs. These triple acting prodrugs are referred to herein as "tetrapartate" prodrugs because the inventive conjugates are provided in essentially four parts.

With the tetrapartate prodrugs of the invention, a therapeutic or diagnostic agent that is delivered to the bloodstream by the above-described double prodrug transport system, will essentially remain inactive until entering or being actively transported into a target cell of interest, whereupon it is activated by intracellular chemistry, e.g., by an enzyme or enzyme system present in that tissue or cell.

In particular, it has now been discovered that when certain types of additional moieties are linked to the biologically active material as part of the above described double prodrug conjugates, the effectiveness of many such biologically active materials is markedly increased, relative to the effectiveness seen with analogous prodrugs that lack such additional moiety. The tetrapartate prodrug conjugates of the invention are thought to provide enhanced effectiveness, e.g., for therapeutic and/or diagnostic activity, in the delivery and activity of certain biologically active materials, e.g., particularly small molecule therapeutic and diagnostic agents. The tetrapartate prodrugs of the invention are prepared so that in vivo hydrolysis of the polymer-based conjugate cleaves the conjugate so as to release the active biological material into extracellular fluid, while still linked to the additional moiety. The biologically active materials are preferably, but not exclusively, small molecule therapeutic and/or diagnostic agents. As exemplified below, in one preferred embodiment these are small molecule anti-cancer agents, and the tissue to be treated is tumor tissue.

Without intending to be bound by any theory or hypothesis as to how the invention might operate, it is believed that, depending upon the additional moiety selected as a transport enhancer, the rate of transport of a biologically active material into tumor cells is by the delivery of a biologically active material into extracellular tissue space, e.g., of a tissue exhibiting an EPR effect, in a protected and/or transport-enhanced form. For convenience in description, the "additional moiety(s)" as mentioned are described herein as, "transport enhancers."

However, in providing this convenient descriptive term, it is not intended to limit the scope of the invention solely to added moieties that solely enhance transport of biologically active materials into targeted cells, since it is believed that additional or alternative mechanisms, such as protection of the Z—[D]$_y$ from extracellular hydrolytic enzyme activity, may contribute to the advantages of the inventive tetrapartate prodrug.

In a further still option, the transport enhancer is selected from among known substrates for a cell membrane transport system. Simply by way of example, cells are known to actively transport certain nutrients and endocrine factors, and the like, and such nutrients, or analogs thereof, are readily employed to enhance active transport of a biologically effective material into target cells. Examples of these nutrients include amino acid residues, peptides, e.g., short peptides ranging in size from about 2 to about 10 residues or more, simple sugars and fatty acids, endocrine factors, and the like.

Desirable amino acid residues include all of the known naturally-occurring L-amino acids. For example, L-isoleucine as a transport enhancer is exemplified in the Examples provided below. Surprisingly, it has also been discovered that D-amino acids are useful as transport enhancers, e.g., both D and L-alanine, and other analogous amino acid optical isomers, show the same activity. Derivatives and analogs of the naturally occurring amino acids, as well as various art-known non-naturally occurring amino acids (D or L), hydrophobic or non-hydrophobic, are also contemplated to be within the scope of the invention. Simply by way of example, amino acid analogs and derivates include: 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2-diaminopimelic acid, 2,3-diaminopropionic acid, n-ethylglycine, N-ethylasparagine, 3-hydroxyproline, 4-hydroxyproline, isodesmosine, allo-isoleucine, N-methylglycine, sarcosine, N-methylisoleucine, 6-N-methyl-lysine, N-methylvaline, norvaline, norleucine, ornithine, and others too numerous to mention, that are listed in 63 Fed. Reg., 29620, 29622, incorporated by reference herein.

Short peptides are, for example, peptides ranging from 2 to about 10, or more, amino acid residues, as mentioned supra. In this embodiment of the invention, it is believed that such peptide transport enhancers need not be hydrophobic, but are thought to function in other ways to enhance uptake and/or to protect the linked small molecule agents from premature hydrolysis in the general bloodstream. For instance, peptide transport enhancers, and other transport enhancers of similar molecular weight ranges, are thought to sterically hinder cleavage from the biologically active agent by plasma-based hydrolytic enzymes, but are then cleaved within a target cell by various peptides and/or proteases, such as cathepsins.

Preferably, the transport enhancer is a hydrophobic moiety. Without meaning to be bound to any theory or hypothesis as to how hydrophobicity contributes to efficacy, it is believed that a hydrophobic moiety inhibits the extracellular cleavage of the transport enhancer away from the active biological agent, by inhibiting the attack of hydrolytic enzymes, etc. present in the extracellular tissue space, e.g., in the plasma. Thus, preferred transport enhancers include, e.g., hydrophobic amino acids such as alanine, valine, leucine, isoleucine, methionine, proline, phenylalanine, tyrosine, and tryptophane, as well as non-naturally occurring derivatives and analogs thereof, as mentioned supra.

In a further option, the transport enhancer is a hydrophobic organic moiety. Simply by way of example, the organic moiety is a $C_{6-18}$, or larger, alkyl, aryl or heteroaryl-substituted or nonsubstituted. The organic moiety transport enhancer is also contemplated to encompass and include organic functional groups including, e.g., —C(=S), —C(=O) and/or —C(=NR$_8$), wherein R$_8$ is selected from the same group as that which defines R$_2$, e.g. hydrogen, $C_{1-6}$ alkyls, etc.

In order to appreciate the nature of the invention, several definitions and explanations are provided as follows. The term, "tetrapartate" refers to prodrug conjugates, and in particular, to conjugates incorporating the features of the double prodrugs, as discussed supra, and an additional moiety serving as a transport enhancer positioned between the residue of the biologically active compound and the polymer moiety to form a 4-part structure wherein the biologically active agent is the fourth part of the conjugate. This structure provides that the residue of the biologically active compound is optimized for transport and release substantially into a target cell. The fourth element of the "tetrapartate" is therefore the residue of the biologically active compound, itself Further, diagnostic tetrapartate conjugates incorporating detectable tags are also contemplated, and the use of the terms, "tetrapartate prodrug," or simply, "prodrug" herein, with reference to the inventive conjugates, broadly also includes conjugates and methods of making and delivering diagnostic reagents, including tagged drugs, as well, unless otherwise specified or distinguished.

For purposes of the present invention, the terms, "biologically active material," and "biologically active compound," and/or "biologically active agent," etc., are used interchangeably unless otherwise stated. These terms refer, for example, to a drug or pharmaceutical, and/or a diagnostic agent or reagent, such as a detectable label or marker. The terms "drug," "agent," "medicinal agent," and "active agent" herein refer to compound(s) with useful activity, particularly when administered to an animal, in vivo, and/or to precursors of the same, unless otherwise stated.

As noted in the previous lines, biological activity is any property of such a material or compound that is useful in an animal or person, e.g., for medical, and/or diagnostic purposes. Preferably, the biological activity is manifested in the intracellular space, i.e., the drug or diagnostic agent preferably but not exclusively is useful once delivered/released into the cytoplasm and/or nucleus of one or more types of target cell of interest.

For purposes of the present invention, the use of the singular or plural is not meant to be limiting of the numerical number of the referenced item or object. Thus, the use of the singular to refer to a cell, polymer or drug does not imply that only one cell is treated, only one molecule is prepared or employed, and/or only one drug is employed, and the use of the plural does not exclude application to a single referenced item, unless expressly stated. Further to this point, for purposes of the present invention, the terms, "cell," "cell type," "target cell," and etc., are used interchangeably unless otherwise specified and refer to both singular and plural cells, however organized into a tissue, tissues or other system or component, normal or pathological, of an animal or patient to be treated.

For purposes of the present invention, the term "residue" shall be understood to mean that portion of a biologically active compound which remains after it has undergone a reaction in which the prodrug carrier portion has been attached by modification of e.g., an available hydroxyl or amino group, to form, for example, an ester or amide group, respectively.

For purposes of the present invention, the term "alkyl" shall be understood to include, e.g., straight, branched, substituted $C_{1-12}$ alkyls, including alkoxy, $C_{3-8}$ cycloalkyls or substituted cycloalkyls, etc.

For purposes of the present invention, the term "substituted" shall be understood to include adding or replacing one or more atoms contained within a functional group or compound with one or more different atoms.

For purposes of the present invention, substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as naphthyl; substituted aryls include moieties such as 3-bromo-phenyl; aralkyls include moieties such as toluyl; heteroalkyls include moieties such as ethylthiophene; substituted heteroalkyls include moieties such as 3-methoxy-thiophene; alkoxy includes moieties such as methoxy; and phenoxy includes moieties such as 3-nitrophenoxy. Halo-shall be understood to include fluoro, chloro, iodo and bromo.

The term "sufficient amounts" for purposes of the present invention shall mean an amount which achieves a therapeutic effect as such effect is understood by those of ordinary skill in the art.

When the prodrugs of the present invention include the double prodrugs taught by co-owned U.S. Pat. No. 6,303,569 and U.S. Pat. No. 5,965,119, it is generally preferred that the polymeric portion is first released by hydrolysis and then the resultant "second prodrug" moiety undergoes a trimethyl lock type elimination reaction to regenerate, for example, a moiety comprising a further prodrug. Thereafter, the released moiety diffuses and/or is transported into target cells, where a substantial proportion of the incorporated remainder of the prodrug is further cleaved or hydrolyzed by intracellular enzymes to release the biologically active compound.

In addition, the terms "cancer" or "tumor" are clinically descriptive terms which encompass a myriad of diseases characterized by cells that exhibit unchecked and abnormal cellular proliferation. The term "tumor", when applied to tissue, generally refers to any abnormal tissue growth, i.e., excessive and abnormal cellular proliferation. The term "cancer" is an older term which is generally used to describe a malignant tumor or the disease state arising therefrom. Alternatively, the art refers to an abnormal growth as a neoplasm, and to a malignant abnormal growth as a malignant neoplasm. These general clinical terms, when used with reference to cells, tissues, and/or one or more conditions characterized as a disease or disorder, as used herein, are intended to be interchangeable and synonymous, unless otherwise specified.

B. Formula (I)

In one preferred embodiment of the invention, there are provided compounds of the formula:

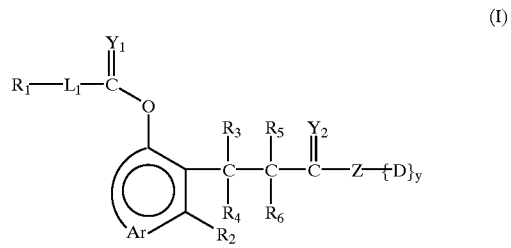

wherein:

$R_1$ is a mono- or bivalent polymer residue, e.g., having a number average molecular weight of from about 2,000 to about 100,000 Daltons;

$L_1$ is a bifunctional linking group;

$Y_1$ and $Y_2$ are independently O, S or $NR_7$;

$R_{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Ar is a moiety which when included in Formula (I) forms a multi-substituted aromatic hydrocarbon or a multi-substituted heterocyclic group; and Broadly, D is a moiety that is a leaving group, or a residue of a compound to be delivered into a cell. More particularly, D is a residue of an active biological material, or H and (y) is a positive integer equal to 1 or greater. Preferably, (y) ranges from 1 to about 5. When (y) is greater than 1, each D moiety is independently selected.

D can be any biologically active material that it is desired to deliver into a target cell or cells of an animal in need of such treatment, including anti-inflammatory agents, detoxifying agents, anticancer agents, and diagnostics for any of these or other conditions.

Preferably, D is an anticancer agent, an anticancer prodrug, a detectable tag, and combinations thereof Any anticancer agent or suitable tag that can be linked to the tetrapartate prodrug is contemplated. Simply by way of example, these include an anthracycline compound, a topoisomerase I inhibitor, daunorubicin, doxorubicin; p-aminoaniline to name but a few.

When D is a leaving group, D can be, e.g. N-hydroxybenzotriazolyl, halogen, N-hydroxyphthalimidyl, p-nitrophenoxy, imidazolyl, N-hydroxysuccinimidyl, thiazolidinyl thione and/or other art recognized leaving groups.

The artisan will appreciate that each D can be selected independently, so that there can be as many as five, or more, different types of moieties linked to Z for delivery into a target cell of interest. Preferably, D is a therapeutic agent or drug, but D is also optionally a diagnostic agent.

Simply by way of illustration, and in certain additional optional embodiments, y is 2 and Z is divalent, D can be two moieties, including both a therapeutic agent and a diagnostic tag for delivery into the same cell type or into the cells of a tissue type of interest. Further still, such plural D moieties will comprise multiple different therapeutic agents, preferably targeted to a single type of cell, where when delivered and released together, the different agents act synergistically to achieve a desired therapeutic effect. In one preferred optional embodiment, D is one or more anticancer agent(s) and/or an anticancer prodrug, or residue thereof In certain further embodiments, D is H, or

wherein B is H, a leaving group, a residue of an amine-containing moiety, or a residue of a hydroxyl-containing moiety and $Y_4$ is selected from the same group as that which defines $Y_1$;

Z is covalently linked to $[D]_y$ and is a moiety that is actively transported into a target cell, a hydrophobic moiety or a combination thereof. Optionally, Z is monovalent, multivalent, or more preferably, bivalent, wherein (y) is 1 or 2. Z itself optionally includes an amino acid residue, a sugar residue, a fatty acid residue, a peptide residue, a $C_{6-18}$ alkyl, a substituted aryl, a heteroaryl, —C(=O), —(=S), and —C(=NR$_{12}$), where $R_{12}$ is selected from the same group which defines $R_2$ and/or combinations thereof.

When Z includes at least one amino acid residue, the amino acid is, e.g., alanine, valine, leucine, isoleucine, glycine, serine, threonine, methionine, cysteine, phenylalanine, tyrosine, tryptophan, aspartic acid, glutamic acid, lysine, arginine, histidine, proline, and/or a combination thereof, to name but a few. When Z includes a peptide, the peptide ranges in size, for instance, from about 2 to about 10 amino acid residues. In one preferred embodiment, the peptide is Gly-Phe-Leu-Gly (SEQ ID NO:1) or Gly-Phe-Leu.

In a further embodiment, Z is a transport enhancer and/or protector that is covalently linked to D, wherein Z is selected to enhance or improve intracellular delivery of Z—[D]y into a cell; relative to the intracellular delivery of D without Z.

As defined in Formula (I), $L_1$ is a bifunctional linker. In particular, $L_1$ is a moiety which facilitates attachment of the polymeric residue to the cyclization or trimethyl lock portion of the platform. Two particularly preferred types of bifunctional linkers are shown below:

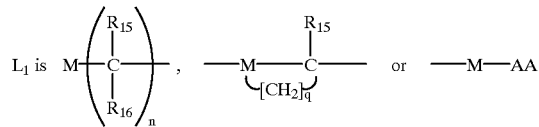

wherein

M is X or Q; wherein
X is an electron withdrawing group
Q is a moiety containing a free electron pair positioned three to six atoms from C(=$Y_2$);

AA is an amino acid residue, preferably of the formula

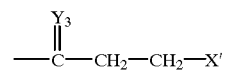

wherein X' is O, S or NR$_{17}$, (n) is zero or a positive integer, preferably 1 or 2;

(q) is three or four; and $R_{15}$, $R_{16}$ and $R_{17}$ are independently selected from the group which defines $R_2$. Specific bifunctional linkers are shown in the examples and in the preferred compounds shown below.

C. Description of the Ar Moiety

Referring to Formula (I), it can be seen that the Ar is a moiety, which when included in Formula (I), forms a multi-substituted aromatic hydrocarbon or a multi-substituted heterocyclic group. A key feature is that the Ar moiety is aromatic in nature. Generally, to be aromatic, the π electrons must be shared within a "cloud" both above and below the plane of a cyclic molecule. Furthermore, the number of π electrons must satisfy the Hückle rule (4n+2). Those of ordinary skill will realize that a myriad of moieties will satisfy the aromatic requirement of the moiety and thus are suitable for use herein. One particularly preferred aromatic group is:

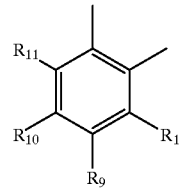

wherein $R_2$ is as defined above and $R_{9-11}$ are selected from the same group which defines $R_2$. Alternative aromatic groups include:

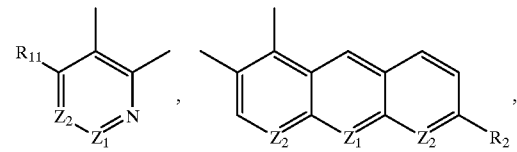

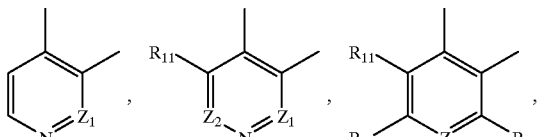

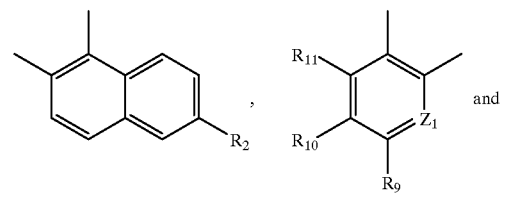

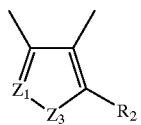

wherein $Z_1$ and $Z_2$ are independently $CR_{23}$ or $NR_{24}$; and $Z_3$ is O, S or $NR_{25}$ where $R_{23-25}$ are selected from the same group as that which defines $R_2$ or a cyano, nitro, carboxyl, acyl, substituted acyl or carboxyalkyl. Isomers of the five and six-membered rings are also contemplated as well as benzo- and dibenzo-systems and their related congeners are also contemplated. It will also be appreciated by the artisan of ordinary skill that the aromatic rings can optionally be substituted with hetero-atoms such as O, S, $NR_{14}$, etc. so long as Hückel's rule is obeyed. Furthermore, the aromatic or heterocyclic structures may optionally be substituted with halogen(s) and/or side chains as those terms are commonly understood in the art. However, all structures suitable for Ar moieties of the present invention are capable of allowing the ortho arrangement with the same plane.

D. Drug Generation Via Hydrolysis of the Prodrug

The prodrug compounds of the present invention are designed so that the $t_{1/2}$ of hydrolysis is $<t_{1/2}$ elimination in plasma. The linkages included in the compounds have hydrolysis rates in the plasma of the mammal being treated which is short enough to allow sufficient amounts of the single prodrug containing a parent compound, i.e. Z—$\{D\}_y$, to be released prior to elimination. Some preferred compounds of the present invention have a $t_{1/2}$ for hydrolysis in plasma ranging from about 5 minutes to about 12 hours. Preferably, the compositions have a plasma $t_{1/2}$ hydrolysis ranging from about 0.5 to about 8 hours and most preferably from about 1 to about 6 hours.

Once the hydrolysis of the double prodrug portion of the conjugate has taken the place in vivo, usually via esterase activity or pH moderated activity or cyclization reaction, the polymeric residue is cleaved and the resultant second prodrug moiety remains.

Without meaning to be bound by any theory or hypothesis as to how the tetrapartate conjugates or prodrugs of the invention operate, it is believed that once the biologically effective material as linked to the uptake enhancer designated herein as Z, enters a target cell, various intracellular peptidases and/or proteases, including e.g., cathepsins, cleave, e.g., by enzymatic hydrolysis, the transport enhancer moiety to release the biologically effective material within the target cell.

The degradation of the tetrapartate prodrug (of formula I) begins with the hydrolysis of the $R_1$-$L_1$ portion at a controllable rate in vivo, to yield the product of formula I(i) (see above). The remaining compound, e.g. I(i), substantially immediately undergoes a tri-methyl lock-type hydrolysis in the presence of water (extracellular) to release the enhancer-prodrug moiety I(iii) from I(ii) mostly into the extracellular tissue space as Z—$[D]_y$. Z—$[D]_y$ is, in turn, taken up by surrounding cells and hydrolyzed intracellularly to release $[D]_y$.

E. Substantially Non-antigenic Polymers

The "tetrapartate prodrug" compositions of the present invention include water-soluble polymer, $R_1$. Optionally, $R_1$ includes a capping group A. Capping group A includes, for example, hydrogen, $C_{1-6}$ alkyl moieties, carboxyalkyl, dialkyl acyl urea alkyls, and/or a compound of formula (V) shown below, which forms a bis-system:

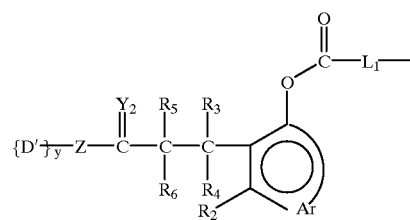

wherein D' is the same as D or another member of the group defined by D, and the remaining variables are as set forth above with regard to Formula (I).

As stated above, $R_1$ is a polymeric residue which is preferably substantially non-antigenic. In preferred aspects of the invention, $R_1$ further includes the previously mentioned capping group A which allows the bis system to be formed. Suitable examples of such polymers include polyalkylene oxides such as polyethylene glycols. The general formula for PEG and its derivatives, i.e.

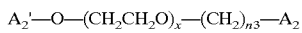

where (x) represents the degree of polymerization (i.e. from about 10 to about 2,300) or number of repeating units in the polymer chain and is dependent on the molecular weight of the polymer, (n3) is zero or a positive integer, ($A_2$) is a capping group as defined herein, i.e. an amino, carboxy, halo, $C_{1-6}$ alkyl or other activating group and ($A'_2$) is the same as ($A_2$) or another ($A_2$) moiety. Also useful are polypropylene glycols, branched PEG derivatives such as those described in commonly-assigned U.S. Pat. No. 5,643,575, "star-PEG's" and multi-armed PEG's such as those described in Shearwater Polymers, Inc. catalog "Polyethylene Glycol Derivatives 1997–1998". The disclosure of each of the foregoing is incorporated herein by reference. It will be understood that the water-soluble polymer can be functionalized for attachment to the linkage via M, herein. As an example, the PEG portion of the inventive compositions can be one of the following non-limiting compounds:

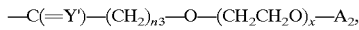

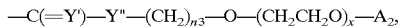

and

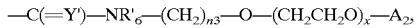

where Y' and Y" are independently O or S and $A_2$, (n3) and (x) are as defined above and $R'_6$ is selected from the same group which defines $R_6$.

In many aspects of the present invention, bis-activated polyethylene glycols are preferred when di-or more substituted polymer conjugates are desired. Alternatively, polyethylene glycols (PEGs), mono-activated, $C_{1-6}$ alkyl-terminated PAO's such as mono-methyl-terminated polyethylene glycols (mPEG's) are preferred when mono-substituted polymers are desired.

In order to provide the desired hydrolyzable linkage, mono- or di-acid activated polymers such as PEG acids or PEG diacids can be used as well as mono- or di-PEG amines and mono- or di-PEG diols. Suitable PAO acids can be synthesized by first converting mPEG-OH to an ethyl ester followed by saponification. See also Gehrhardt, H., et al. *Polymer Bulletin* 18: 487 (1987) and Veronese, F. M., et al., *J. Controlled Release* 10; 145 (1989). Alternatively, the PAO-acid can be synthesized by converting mPEG-OH into a t-butyl ester followed by acid cleavage. See, for example, commonly assigned U.S. Pat. No. 5,605,976. The disclosures of each of the foregoing are incorporated by reference herein.

Although PAO's and PEG's can vary substantially in number average molecular weight, polymers ranging from about 2,000 to about 100,000 are usually selected for the purposes of the present invention. Molecular weights of from about 5,000 to about 50,000 are preferred and 20,000 to about 40,000 are particularly preferred. The number average molecular weight of the polymer selected for inclusion in the prodrug must be sufficient so as to provide sufficient circulation of the prodrug before hydrolysis of the linker. Within the ranges provided above, polymers having molecular weight ranges of at least 20,000 are preferred for chemotherapeutic and organic moieties.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained.

As an alternative to PAO-based polymers, effectively non-antigenic materials such as dextran, polyvinyl alcohols, carbohydrate-based polymers, hydroxypropylmethacrylamide (HPMA), and copolymers thereof etc. and the like can be used if the same type of activation is employed as described herein for PAO's such as PEG. Those of ordinary skill in the art will realize that the foregoing list is merely illustrative and that all polymeric materials having the qualities described herein are contemplated. For purposes of the present invention, "effectively non-antigenic" and "substantially non-antigenic" shall be understood to include all polymeric materials understood in the art as being substantially non-toxic and not eliciting an appreciable immune response in mammals.

It will be clear from the foregoing that other polyalkylene oxide derivatives of the foregoing, such as the polypropylene glycol acids, etc., as well as other bi-functional linking groups are also contemplated.

F. Prodrug Candidates

1. Residues of Biologically Active Materials

Broadly, the only limitations on the types of biologically effective materials suitable for inclusion herein is that there is available at least one site for covalent attachment to the uptake enhancer moiety. Simply by way of example, this can be a (primary or secondary) amine-containing position or functional group which can react and link with a carrier portion, e.g., by forming an amide bond. Other sites for covalent attachment to the uptake enhancer moiety include, e.g., a hydroxyl functional group, to form, e.g., an ester linkage. Of course, the artisan will appreciate that the selected linkage between the biologically effective material of interest, and the uptake enhancer is such that there is no substantial loss of bioactivity after the double prodrug portion of the conjugate releases the parent compound in linkage with a transport enhancer.

After conjugation, the remaining portion of the parent compound is referred to as the residue of the unconjugated compound.

2. Residues of Hydroxyl-containing Compounds a. Camptothecin and Related Topoisomerase I Inhibitors Camptothecin is a water-insoluble cytotoxic alkaloid produced by *Camptotheca accuminata* trees indigenous to China and *nothapoytes foetida* trees indigenous to India. Camptothecin and related compounds and analogs are also known to be potential anticancer or antitumor agents and have been shown to exhibit these activities in vitro and in vivo. Camptothecin and related compounds are also candidates for conversion to the prodrugs of the present invention. Camptothecin and certain related analogues share the structure:

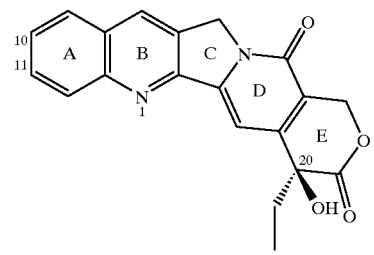

From this core structure, several known analogs have been prepared. For example, the A ring in either or both of the 10- and 11-positions can be substituted with an OH. The A ring can also be substituted in the 9-position with a straight or branched $C_{1-30}$ alkyl or $C_{1-17}$ alkoxy, optionally linked to the ring by a heteroatom i.e. —O or S. The B ring can be substituted in the 7-position with a straight or branched $C_{1-30}$ alkyl or substituted alkyl-, $C_{5-8}$ cycloakyl, $C_{1-30}$ alkoxy, phenyl alkyl, etc., alkyl carbamate, alkyl carbazides, phenyl hydrazine derivatives, amino-, aminoalkyl-, aralkyl, etc. Other substitutions are possible in the C, D and E rings. See, for example, U.S. Pat. Nos. 5,004,758; 4,943,579; Re 32,518, the contents of which are incorporated herein by reference. Such derivatives can be made using known synthetic techniques without undue experimentation. Preferred camptothecin derivatives for use herein include those which include a 20-OH or another OH moiety which is capable of reacting directly with activated forms of the polymer transport systems described herein or to the linking moiety intermediates, e.g. iminodiacetic acid, etc., which are then attached to a polymer such as PEG. Reference to camptothecin analogs herein has been made for purposes of illustration and not limitation.

b. Taxanes and Paclitaxel Derivatives

One class of compounds included in the prodrug compositions of the present invention is taxanes. For purposes of the present invention, the term "taxane" includes all compounds within the taxane family of terpenes. Thus, taxol (paclitaxel), 3'-substituted tert-butoxy-carbonyl-amine derivatives (taxoteres) and the like as well as other analogs which are readily synthesized using standard organic techniques or are available from commercial sources such as Sigma Chemical of St. Louis, Mo. are within the scope of the present invention. These derivatives have been found to be effective anti-cancer agents. Numerous studies indicate that the agents have activity against several malignancies. To date, their use has been severely limited by, among other things, their short supply, poor water solubility and a tendency to cause hypersensitivity. It is to be understood that other taxanes including the 7-aryl-carbamates and 7-carbazates disclosed in commonly assigned U.S. Pat. Nos. 5,622,986 and 5,547,981 can also be included in the prodrugs of the present invention. The contents of the foregoing U.S. patents are incorporated herein by reference. Paclitaxel is a preferred taxane.

c. Additional Biologically-Active Moieties

In addition to the foregoing molecules, the prodrug formulations of the present invention can be prepared using many other compounds. For example, biologically-active compounds such as bis-PEG conjugates derived from compounds such as gemcitabine:

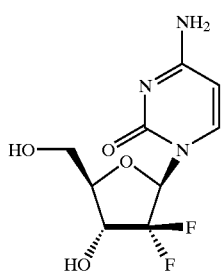

or podophyllotoxin:

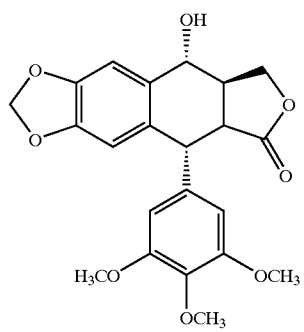

or triazole-based antifingal agents such as fluconazole:

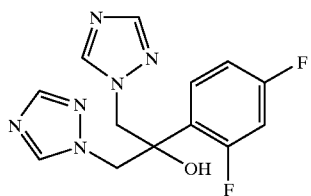

or ciclopirox:

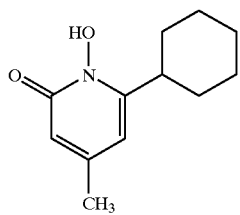

or Ara-C:

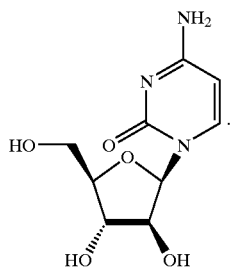

The parent compounds selected for prodrug forms need not be substantially water-insoluble, although the polymer-based prodrugs of the present invention are especially well suited for delivering such water-insoluble compounds. Other useful parent compounds include, for example, certain low molecular weight biologically active proteins, enzymes and peptides, including peptido glycans, as well as other anti-tumor agents; cardiovascular agents such as forskolin; anti-neoplastics such as combretastatin, vinblastine, doxorubicin, maytansine, etc.; anti-infectives such as vancomycin, erythromycin, etc.; anti-fungals such as nystatin, amphotericin B, triazoles, papulocandins, pneumocandins, echinocandins, polyoxins, nikkomycins, pradimicins, benanomicins, etc. see, "Antibiotics That Inhibit Fungal Cell Wall Development" Annu. Rev. Microbiol. 1994, 48:471–97, the contents of which are incorporated herein by reference; anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active moieties which are suitable for the prodrugs of the present invention. It is to be understood that those biologically active materials not specifically mentioned but having suitable ester-forming groups, i.e. hydroxyl moieties, are also intended and are within the scope of the present invention. It is also to be understood that the prodrug conjugates of the present invention may also include minor amounts of compounds containing not only one equivalent of drug and polymer but also a moiety which does not effect bioactivity in vivo. For example, it has been found that in some instances, in spite of reacting diacids with drug molecules having a single linkage point, the reaction conditions do not provide quantitative amounts of prodrugs with two equivalents of drug per polymer. By-products of the reactants can sometimes be formed such as acyl ureas if carbodiimides are used.

3. Residues of Amine Containing Compounds

In some aspects of the invention, D is a residue of an amine-containing compound, a non-limiting list of such suitable compounds include residues of organic compounds, enzymes, proteins, polypeptides, etc. Organic compounds include, without limitation, moieties such as anthracycline compounds including daunorubicin, doxorubicin; p-aminoaniline mustard, melphalan, Ara-C (cytosine arabinoside) and related anti-metabolite compounds, e.g., gemcitabine, etc. Alternatively, D can be a residue of an amine-containing cardiovascular agent, anti-neoplastic, anti-infective, anti-fungal such as nystatin and amphotericin B, anti-anxiety agent, gastrointestinal agent, central nervous system-activating agent, analgesic, fertility agent, contraceptive agent, anti-inflammatory agent, steroidal agent, anti-urecemic agent, vasodilating agent, vasoconstricting agent, etc.

In a preferred aspect of the invention, the amino-containing compound is a biologically active compound that is suitable for medicinal or diagnostic use in the treatment of animals, e.g., mammals, including humans, for conditions for which such treatment is desired. The foregoing list is meant to be illustrative and not limiting for the compounds which can be modified. Those of ordinary skill will realize that other such compounds can be similarly modified without undue experimentation. It is to be understood that those biologically active materials not specifically mentioned but having suitable amino-groups are also intended and are within the scope of the present invention.

The only limitations on the types of amino-containing molecules suitable for inclusion herein is that there is available at least one (primary or secondary) amine-containing position which can react and link with a carrier portion and that there is not substantial loss of bioactivity after the prodrug system releases and regenerates the parent compound.

It is noted that parent compounds suitable for incorporation into the prodrug compositions of the invention, may themselves be substances/compounds which are not active after hydrolytic release from the linked composition, but which will become active after undergoing a further chemical process/reaction. For example, an anticancer drug that is delivered to the bloodstream by the double prodrug transport system, may remain inactive until entering a cancer or tumor cell, whereupon it is activated by the cancer or tumor cell chemistry, e.g., by an enzymatic reaction unique to that cell.

4. Leaving Groups

In those aspects where D is a leaving group, suitable leaving groups include, without limitations, moieties such as N-hydroxybenzotriazolyl, halogen, N-hydroxyphthalimidyl, p-nitrophenoxy, imidazolyl, N-hydroxysuccinimidyl; thiazolidinyl thione, or other good leaving groups as will be apparent to those of ordinary skill. The synthesis reactions used and described herein will be understood by those of ordinary skill without undue experimentation.

For example, an acylated intermediate of compound (I) can be reacted with a reactant such as 4-nitrophenyl chloroformate, disuccinimidyl carbonate (DSC), carbonyldiimidazole, thiazolidine thione, etc. to provide the desired activated derivative. The selective acylation of the phenolic or anilinic portion of the p-hydroxybenzyl alcohol or the p-aminobenzyl alcohol and the o-hydroxbenzyl alcohol or the o-aminobenzyl alcohol can be carried out with, for example, thiazolidine thione activated polymers, succinimidyl carbonate activated polymers, carboxylic acid activated polymers, blocked amino acid derivatives. Once in place, the "activated" form of the PEG prodrug (or blocked prodrug) is ready for conjugation with an amine- or hydroxyl-containing compound.

G. Synthesis of the Polymeric Transport System

In one embodiment, the method includes reacting a compound of formula (II):

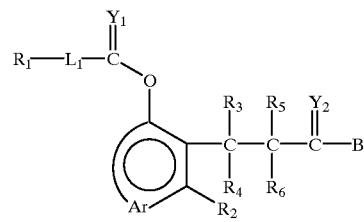

with a compound of the formula (III):

Lx-Z—[D]y;  (III)

wherein B is a leaving group for Formula (II) and is defined as above for when D is a leaving group.

Lx is a leaving group for Formula (III) and is defined as above for when D is a leaving group.

Ar, $R_{1-6}$, $L_1$, $Y_{1-2}$, Z, $\{D\}_y$ and integers are defined as above. The reaction between (II) and (III) is preferably conducted in the presence of a solvent and a base. The solvent is, for example, chloroform, methylene chloride, toluene, dimethylformamide and/or combinations thereof. Dimethylformamide is generally preferred. The base is, for example, dimethylaminopyridine, diisopropylethylamine, pyridine, triethylamine and/or combinations thereof.

Yet another method of preparing a tetrapartate prodrug of the invention is conducted by reacting a compound of formula (IV)

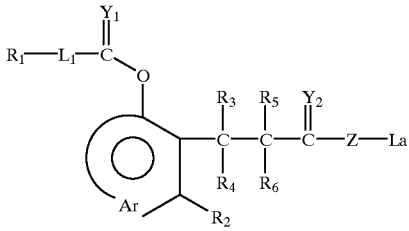

with a biologically active material; wherein

La is a leaving group as defined when D is a leaving group.

Ar, $R_{1-6}$, $L_1$, $Y_{1-2}$, Z, $\{D\}_y$ and integers are defined as above.

Additional compounds of formula IV are synthesized in accordance with the procedures of Greenwald, et al, "Drug Delivery Systems Based on Trimethyl Lock Lactonization: Poly(ethylene glycol) Prodrugs of Amino-Containing Compounds," *J. Med. Chem.*, 2000, Vol. 43, Num. 3, pp. 475–487, the disclosure of which is incorporated herewith.

Optionally, the reaction between (IV) and the biologically active material is conducted in the presence of a coupling agent, e.g., 1,3-diisopropylcarbodiimide, a dialkyl carbodiimides, 2-halo-1-alkyl-pyridinium halide, 1-(3-dimethylaminopropyl)-3-ethyl carbodiimide, 1-propanephosphonic acid cyclic anhydride, phenyl dichlorophosphates, and/or combinations thereof. The reaction between (IV) and the biologically active material is conducted in the presence of a solvent and a base, e.g., as described above for the previous synthetic method.

Regardless of the synthesis selected, some of the preferred compounds which result from the synthesis techniques described herein are found in FIGS. 3–6.

2. Polymeric Hybrids

In another aspect of the invention there are provided hybrid types of the polymeric tetrapartate prodrug transport system described herein. In particular, the hybrid system includes not only the reversible double prodrug system described above but also a second polymeric transport system based on more permanent types of linkages. The hybrids can be prepared by at least two methods. For example, the benzyl-elimination-based prodrug can be synthesized first and then PEGylated using any art-recognized activated polymer such as thiazolidinyl thione-or succinimidyl carbonate-activated PEG. Alternatively, the more permanent conjugation reaction can be performed first and the resultant conjugates can be used to form the double prodrug portion of the tetrapartate conjugates described herein. It will be understood that the hybrid systems will be better suited for proteins, enzymes and the like where multiple amino groups are available for attachment of the polymeric transport forms. For purposes of the present invention, "activated polymers" will be understood to include polymers containing one or more terminal groups which are capable of reacting with one or more of amino groups, histidine nitrogens, carboxyl groups, sulfhydryl groups, etc. found on enzymes, proteins, etc., as well as such groups found on synthetically prepared organic compounds. It will further be appreciated that the activating groups described below can also be used to form the activated transport forms described above.

The activating terminal moiety can be any group which facilitates conjugation of the polymers with the biologically active material, i.e., protein, enzyme, etc. either before of after the double prodrug transport system of the present invention has been synthesized. See, for example, U.S. Pat. No. 4,179,337, the disclosure of which is hereby incorporated by reference. Such activating groups can be a moiety selected from:

I. Functional groups capable of reacting with an amino group such as:
   a) carbonates such as the p-nitrophenyl, or succinimidyl; see, for example, U.S. Pat. No. 5,122,614, the disclosure of which is hereby incorporated by reference;
   b) carbonyl imidazole;
   c) azlactones; see, for example, U.S. Pat. No. 5,321,095, the disclosure of which is hereby incorporated by reference;
   d) cyclic imide thiones see, for example, U.S. Pat. No. 5,349,001, the disclosure of which is hereby incorporated by reference;
   e) isocyanates or isothiocyanates; or
   f) active esters such as N-hydroxy-succinimidyl or N-hydroxybenzotriazolyl.

II. Functional groups capable of reacting with carboxylic acid groups and reactive carbonyl groups such as:
   a) primary amines; or
   b) hydrazine and hydrazide functional groups such as the acyl hydrazides, carbazates, semicarbamates, thiocarbazates, etc.

III. Functional groups capable of reacting with mercapto or sulfhydryl groups such as phenyl glyoxals; see, for example, U.S. Pat. No. 5,093,531, the disclosure of which is hereby incorporated by reference;

IV. Functional groups capable of reacting with hydroxyl groups such as (carboxylic) acids or other nucleophiles capable of reacting with an electrophilic center. A non-limiting list includes, for example, hydroxyl, amino, carboxyl, thiol groups, active methylene and the like.

The activating moiety can also include a spacer moiety located proximal to the polymer. The spacer moiety may be a heteroalkyl, alkoxy, alkyl containing up to 18 carbon atoms or even an additional polymer chain. The spacer moieties can added using standard synthesis techniques.

H. Methods of Treatment

Broadly, another aspect of the present invention provides methods for delivering biologically active materials, such as therapeutic or diagnostic agents into cells where such biological activity is desired. While the tetrapartate prodrugs of the invention are readily employed to deliver biologically active materials into a wide variety of cells, found throughout the animal body, certain applications are preferred. For example, the tetrapartate prodrugs of the invention are particularly useful in delivering biologically active materials, such as drugs and/or diagnostics, into cells present in tissues exhibiting the above-discussed EPR effect. A number of tissue types exhibiting EPR occur in different diseases and disorders, including tissues undergoing inflammation, toxic reactions of various kinds, as well as solid tumors.

Thus, the broad method includes contacting living tissue with the inventive tetrapartate prodrugs. Preferably the tissue exhibits the EPR effect, so that polymer linked conjugates preferably enter such tissues. Of course, the artisan will appreciate that an agent, once delivered into a target cell and activated, can then be released by that cell and provide biological activity in other tissue spaces.

Simply by way of example, a non-active prodrug of the invention that is delivered into an exocrine cell of the liver or pancreas under suitable conditions, e.g., during a disease process that causes inflammation, and results in an EPR effect, can be activated within the cytoplasm of the target cell, and then the activated drug or diagnostic agent can then be secreted into the gastrointestinal ("G.I") tract fluid space for therapeutic and/or diagnostic purposes. In this instance, treatment and/or diagnosis of certain diseases or disorders of the G.I. tract by means of the targeted delivery of appropriate agents, including anti-cancer or antiviral agents, is therefore facilitated. Analogous methods of treatment and delivery of biologically active materials is readily contemplated for other organ and/or tissue systems.

In one preferred embodiment, the tissues are tumor or cancer tissues, and the tetrapartate prodrugs of in the invention comprise agents suitable for treatment and/or diagnosis of such conditions. Thus, the tetrapartate prodrug compositions are useful for, among other things, treating diseases which are similar to those which are treated with the parent compound(s), e.g, including compounds suitable for treating neoplastic disease, reducing tumor burden, inhibiting metastasis of tumors or neoplasms and preventing recurrences of tumor/neoplastic growths in mammals. The treated animals are preferably mammals, and more preferably human patients. While veterinary use of the prodrugs of the invention will typically be employed in mammalian species, it is further contemplated that the prodrugs can also be readily employed in other species generally within the veterinary practice and animal husbandry arts, e.g., including highly valued non-mammalian exotic animals.

The amount of the prodrug and/or diagnostic tetrapartate tag that is administered will depend upon the amount of the parent molecule included therein. Generally, the amount of tetrapartate prodrug used in the treatment methods is that amount which effectively achieves the desired therapeutic or diagnostic result in mammals. Naturally, the dosages of the various prodrug compounds will vary somewhat depending upon the parent compound, rate of in vivo hydrolysis, molecular weight of the polymer, etc. In general, tetrapartate prodrug polymeric derivatives are administered in amounts ranging from about 5 to about 500 mg/m2 per day, based on the native drug. The range set forth above is illustrative and those skilled in the art will determine the optimal dosing of the prodrug selected based on clinical experience and the treatment indication. Actual dosages will be apparent to the artisan without undue experimentation.

The compositions, including prodrugs, of the present invention can be included in one or more suitable pharmaceutical compositions for administration to an animal in need thereof. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan. A solution and/or suspension of the composition may be utilized, for example, as a carrier vehicle for injection or infiltration of the composition by any art known methods, e.g., by intravenous, intramuscular, subdermal injection and the like.

Such administration may also be by infusion into a body space or cavity, as well as by inhalation and/or intranasal routes. In preferred aspects of the invention, however, the prodrugs are parenterally administered to animals in need thereof.

The novel methods of treatment or administration according to the invention further includes the multi-step cleavage of the prodrug, resulting in release of the biologically active material, such as a drug or tag, within a target cell.

I. In vivo Diagnostics

A further aspect of the invention provides the conjugates of the invention optionally prepared with a diagnostic tag linked to the transport enhancer described above, wherein the tag is selected for diagnostic or imaging purposes. Thus, a suitable tag is prepared by linking any suitable moiety, e.g., an amino acid residue, to any art-standard emitting isotope, radio-opaque label, magnetic resonance label, or other non-radioactive isotopic labels suitable for magnetic resonance imaging, fluorescence-type labels, labels exhibiting visible colors and/or capable of fluorescing under ultraviolet, infrared or electrochemical stimulation, to allow for imaging tumor tissue during surgical procedures, and so forth. Optionally, the diagnostic tag is incorporated into and/or linked to a conjugated therapeutic moiety, allowing for monitoring of the distribution of a therapeutic biologically active material within an animal or human patient.

In a still further aspect of the invention, the inventive tagged conjugates are readily prepared, by art-known methods, with any suitable label, including, e.g., radioisotope labels. Simply by way of example, these include $^{131}$Iodine, $^{125}$Iodine, $^{99m}$Technetium and/or $^{111}$Indium to produce radioimmunoscintigraphic agents for selective uptake into tumor cells, in vivo. For instance, there are a number of art-known methods of linking peptide to Tc-99m, including, simply by way of example, those shown by U.S. Pat. Nos. 5,328,679; 5,888,474; 5,997,844; and 5,997,845, incorporated by reference herein.

Broadly, for anatomical localization of tumor tissue in a patient, the conjugate tag is administered to a patient or animal suspected of having a tumor. After sufficient time to allow the labeled immunoglobulin to localize at the tumor site(s), the signal generated by the label is detected, for instance, visually, by X-ray radiography, computerized transaxial tomography, MRI, by instrumental detection of a luminescent tag, by a photo scanning device such as a gamma camera, or any other method or instrument appropriate for the nature of the selected tag. The detected signal is then converted to an image or anatomical and/or physiological determination of the tumor site. The image makes it possible to locate the tumor in vivo and to devise an appropriate therapeutic strategy. In those embodiments where the tagged moiety is itself a therapeutic agents, the detected signal provides evidence of anatomical localization during treatment, providing a baseline for follow-up diagnostic and therapeutic interventions.

J. EXAMPLES

The following examples serve to provide further appreciation of the invention but are not meant in any way to restrict the effective scope of the invention. The underlined and bold-faced numbers recited in the Examples correspond to those shown in FIGS. 1 and 2.

General. All reactions were run under an atmosphere of dry nitrogen or argon. Commercial reagents were used without further purification. All PEG compounds were dried under vacuum or by azeotropic distillation (toluene) prior to use. $^1$H spectra were obtained with a Varian FT NMR instrument using deuteriochloroform as solvent unless specified. $^{13}$C NMR spectra were obtained at 75.45 MHz on the on the Varian MercuryVX-300. Chemical shifts (d) are reported in parts per million (ppm) downfield from tetramethylsilane (TMS) and coupling constants (J values) are given in hertz (Hz). All PEG conjugated compounds were dissolved (~15 mg/mL) in sterile saline (0.9%) for injection prior to in vivo drug treatments and were given as their DOX equivalents (absolute amount of DOX given).

Abbreviations. DCM (dichloromethane), DMAP (4-(dimethylamino)pyridine), EDC (1-ethyl-3-(3-dimethylaminopropyl)carbodiimide), HOBT (1-hydroxybenzotriazole), IPA (2-propanol), NMM (N-methylmorpholine), TFA (trifluoroacetic acid) and ALA-CMPT (20-S-alanine-camptothecin).

Figure 2:
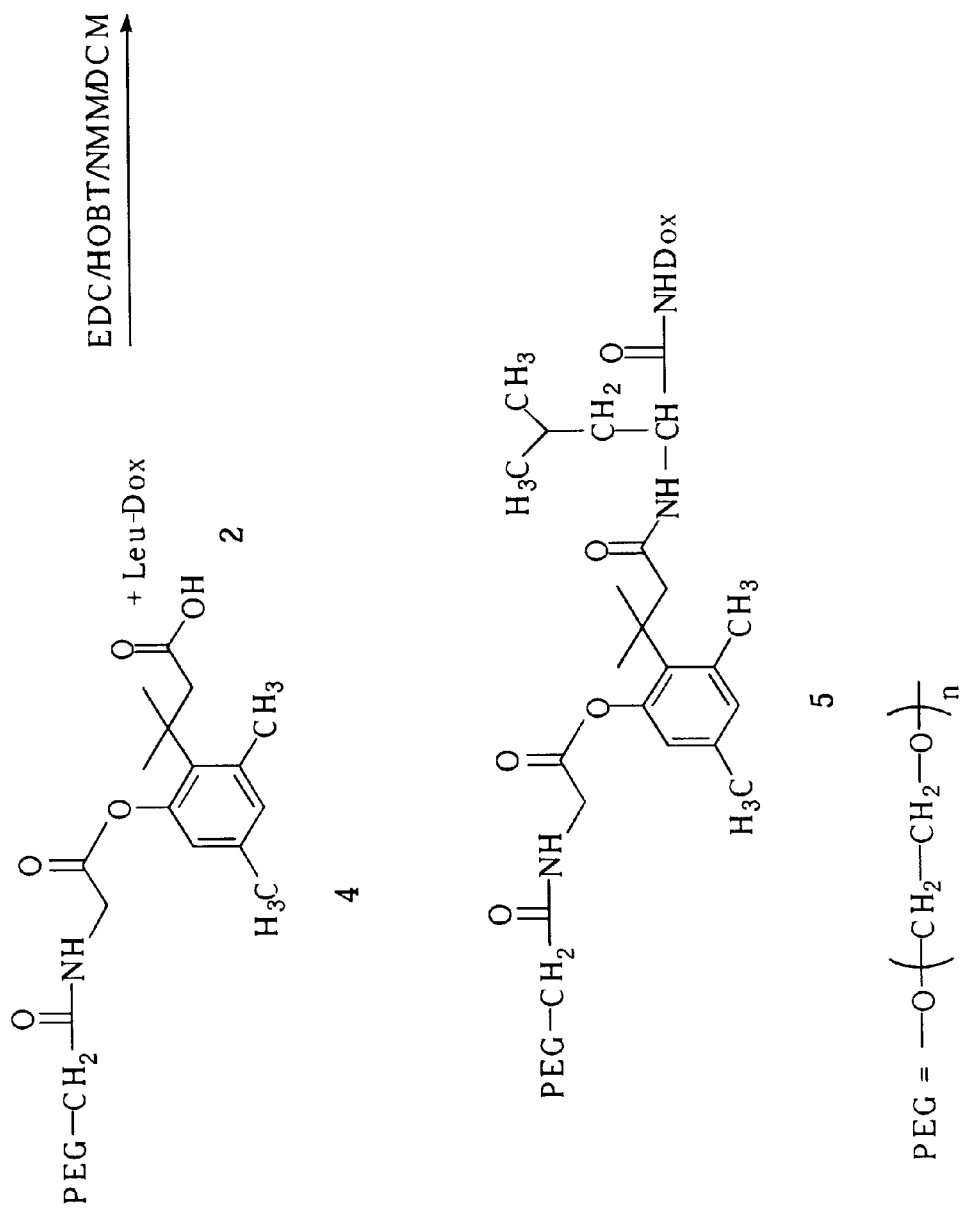
Figure 3:
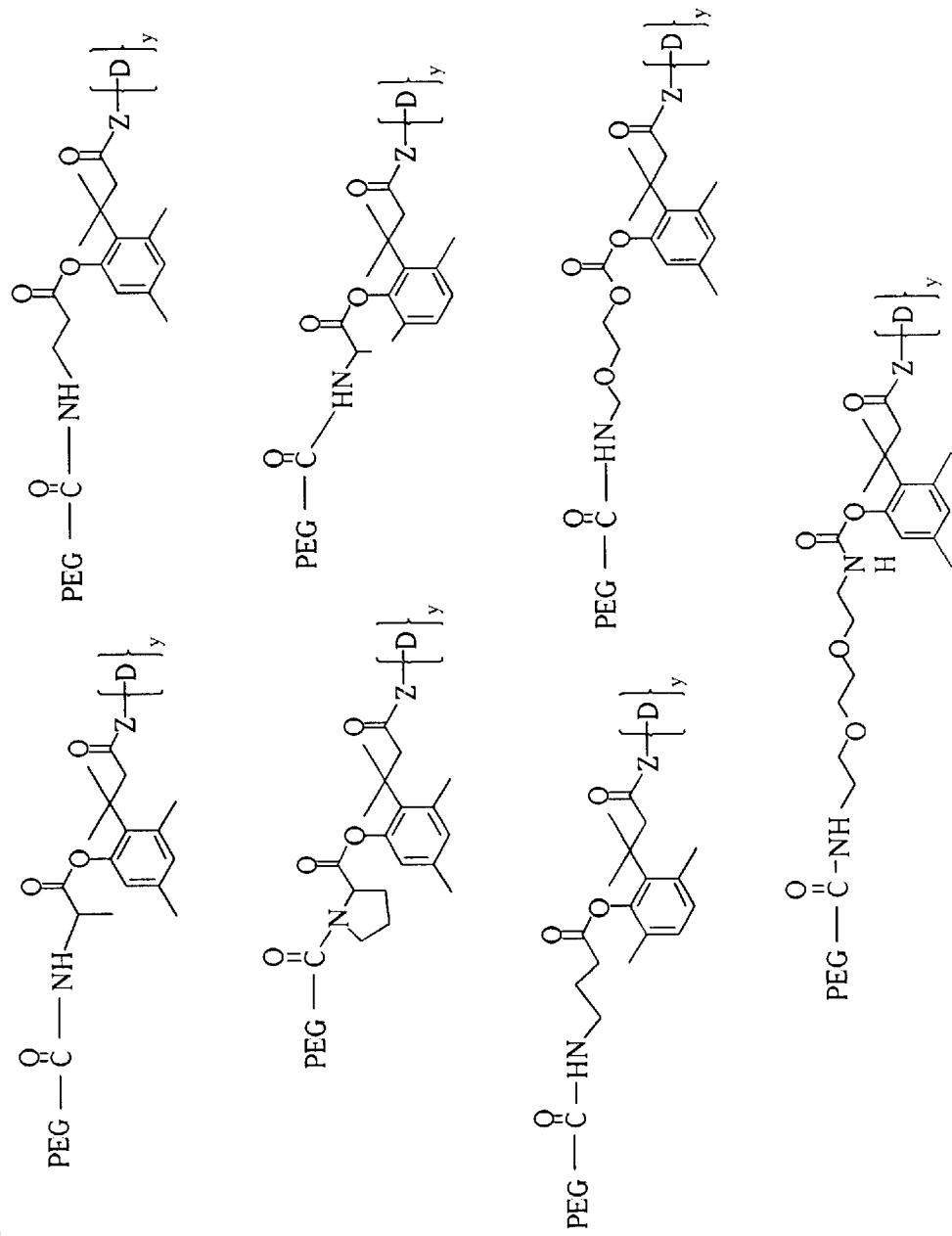
FIGS. 3–6 illustrate compounds prepared in accordance with the present invention.
Figure 4:
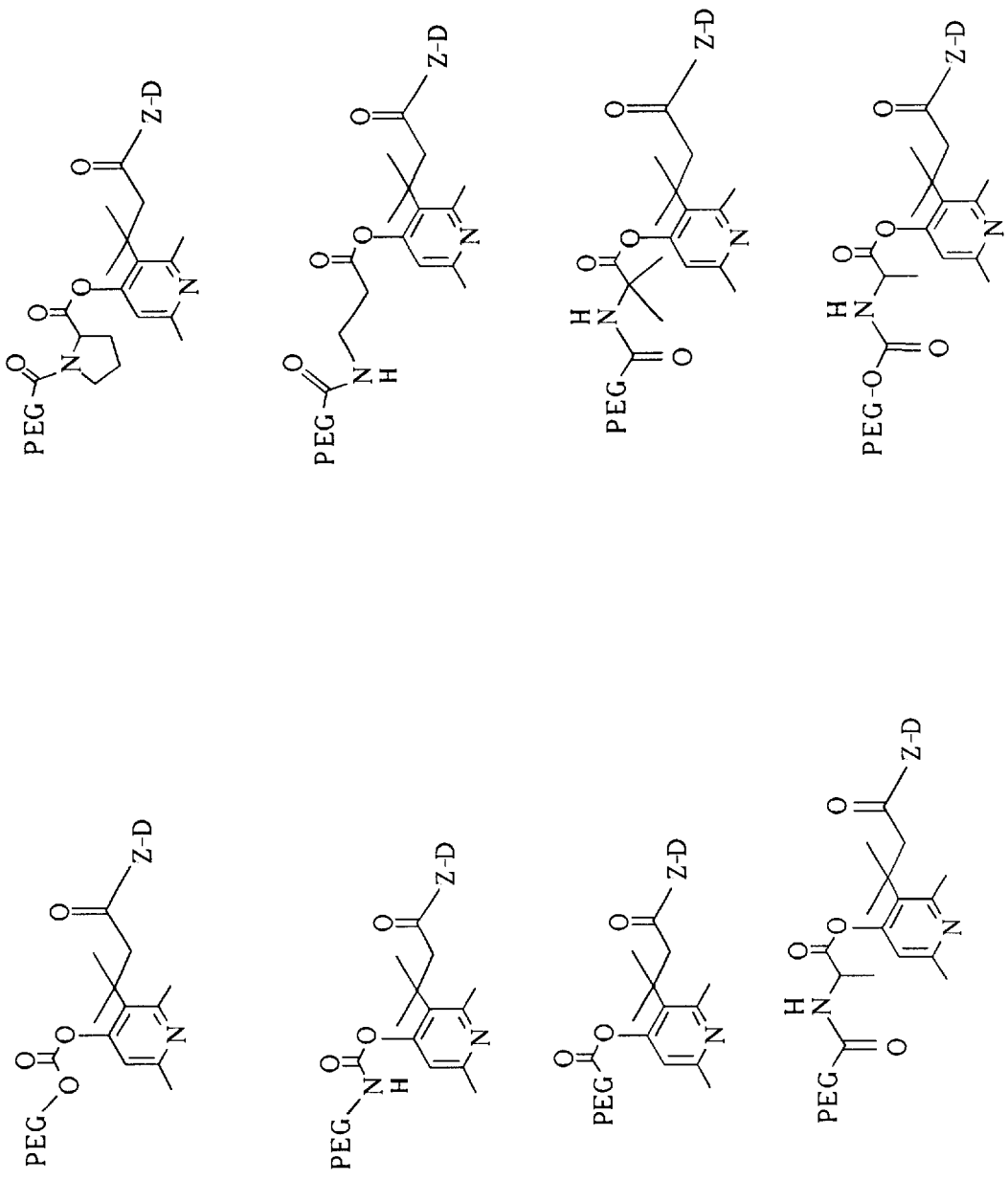
Figure 5:
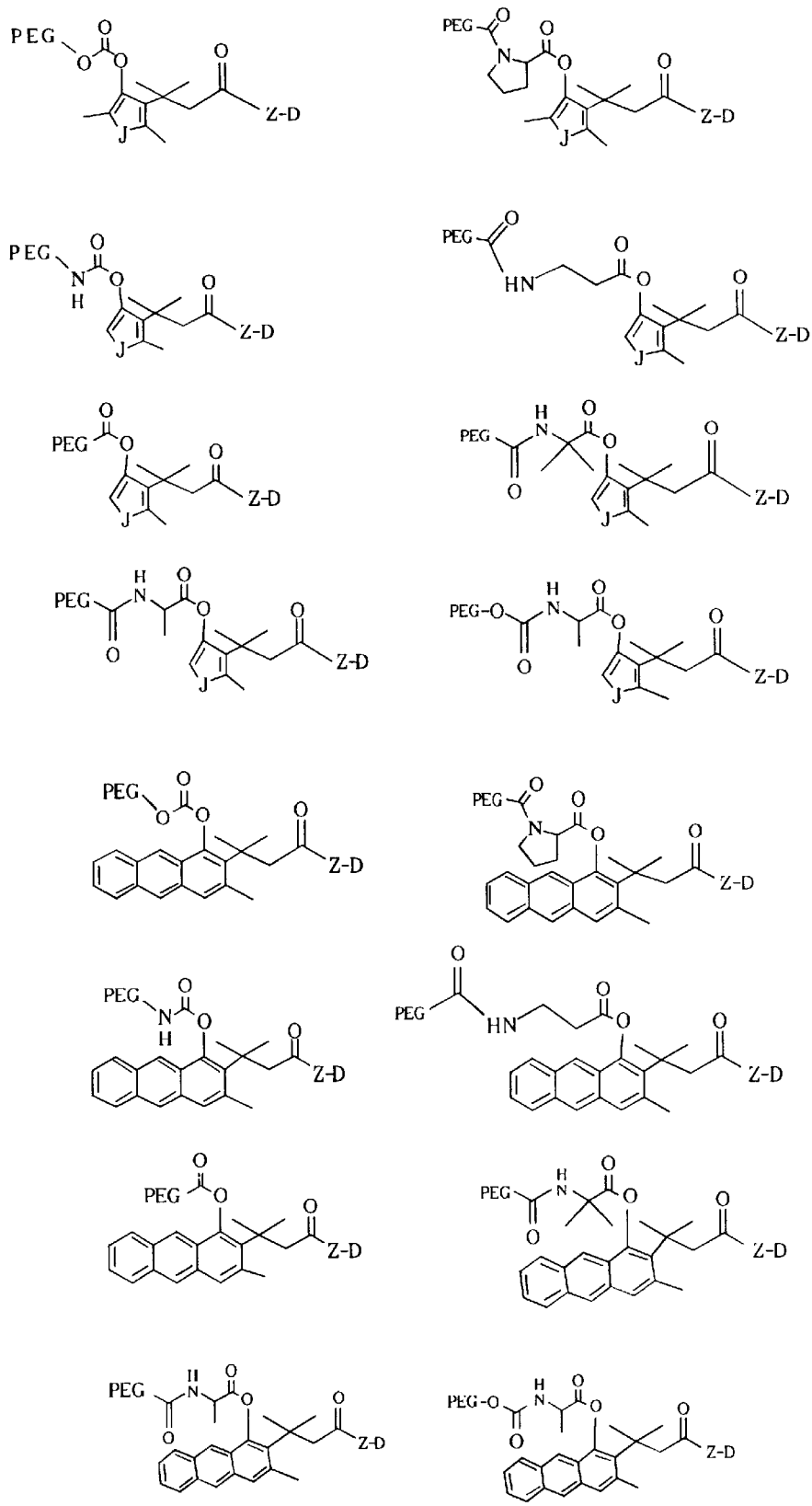
Figure 6:
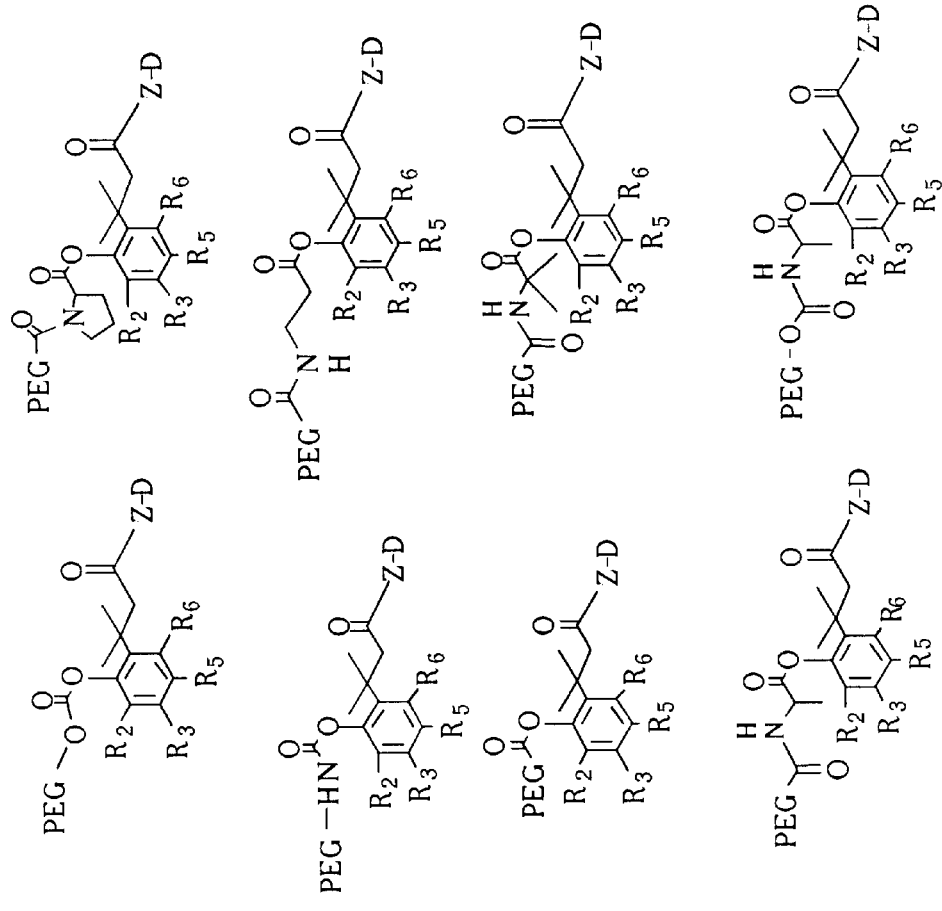

It should be noted for all of the compounds that were produced by the following examples, and as illustrated by FIGS. 1–2, that "PEG" is:

wherein n represents the degree of polymerization. Other art-known variations are readily employed, as mentioned supra.

In addition, the PEG employed in the following examples had a molecular weight of about 40 kDa. The following examples serve to provide further appreciation of the invention but are not meant in any way to restrict the effective scope of the invention.

Example 1a

Compound 3 was prepared as illustrated by FIG. 1. 40 kDa PEG-TML3-Leucine-Doxrubicin 3: To a solution of 40 kDa PEG-TML3-Acid 1 (2.0 g, 0.049 mmol) in 40 mL anhydrous DMF was added Leucine-Doxorubicin 2 (87 mg, 0.132 mmol) and DMAP (97 mg, 0.79 mmol) and the mixture was cooled in an ice-bath to 0 (C. for 20 min. Then EDC (76 mg, 0.396 mmol) was added and the reaction mixture gradually warmed to room temperature and stirred overnight. Ethyl ether (~100 mL) was added to the reaction mixture to precipitate PEG derivatives and the solid obtained by filtration. The solid was recrystallized from IPA twice (60 mL each time) to give pure product 3 (1.91 g, 93%).

The structure was confirmed by $^{13}$C NMR (67.8 MHz, CDCl$_3$) with peaks at d 213.58, 186.72, 186.34, 171.90, 171.42, 170.90, 160.72, 155.96, 155.41, 145.48, 136.68, 135.48, 135.16, 133.59, 131.14, 128.32, 127.88, 126.49, 120.51, 119.47, 118.22, 111.16, 108.67, 100.58, 69.0–72.5 (PEG), 68.49, 67.10, 65.16, 56.35, 52.16, 48.70, 47.72, 47.10, 45.58, 39.89, 39.61, 35.32, 33.63, 32.07, 31.20, 28.90, 25.27, 24.28, 22.72, 21.02, 18.84, 16.63, 16.27.

Example 1b

The procedure of Example 1a is repeated except that Leucine-Doxorubicin is replaced by 20-S-alanine-camptothecin-TFA salt 6 (0.102 g, 0.196 mmol) to yield the final product.

Example 2a

Compound 5 40 kDa PEG-TML1-Leucine-Doxrubicin was prepared as illustrated by FIG. 2. To a solution of 40 kDa PEG-TML1-Acid 4 (1.0 g, 0.025 mmol) in 10 mL anhydrous methylene chloride was added Leucine-Doxorubicin 2 (64 mg, 0.098 mmol), 4-methylmorpholine (NMM 0.396 mmol), 1-hydroxybenzotriazole hydrate (HOBT, 15 mg, 0.098 mmol), and EDC (35 mg, 0.196 mmol). The resulting mixture was stirred at room temperature overnight. Ethyl ether was added to the reaction solution until turbid and the mixture chilled in freezer for 30 min before it was filtered to give the product 5 which was purified by recrystallization from IPA (0.93 g, 90%).

The structure was confirmed by $^{13}$C NMR (67.8 MHz, CDCl$_3$) with peaks at d 213.53, 186.62, 186.24, 172.08, 171.87, 171.72, 170.88, 160.64, 155.89, 155.31, 149.48, 138.54, 135.99, 135.43, 135.06, 133.56, 133.38, 133.33, 132.49, 122.08, 120.41, 119.40, 118.18, 111.06, 110.87, 100.44, 69.0–72.5 (PEG), 68.91, 67.75, 67.04, 65.10, 56.30, 52.11, 48.67, 48.05, 45.26, 39.71, 39.65, 39.35, 35.27, 33.53, 32.03, 31.71, 28.80, 25.30, 23.70, 22.72, 20.89, 19.77, 16.59, 15.92.

Example 2b

The procedure of Example 2a is repeated except that Leucine-Doxorubicin is replaced by 20-S-alanine-camptothecin-TFA salt 6 (0.052 g, 0.100 mmol) to yield the final product.

Example 3a

In this example, the procedure of Example 1a is repeated except that compound 7, TML1β as shown below is used instead of PEG-TML3 acid (1).

Example 3b

The procedure of Example 3a is repeated except that Leucine-Doxorubicin is replaced by 20-S-alanine-camptothecin-TFA salt 6 (0.120 g, 0.196 mmol) to yield the final product.

Example 4a

In this example, the procedure of Example 1 a is repeated except that compound 8, TML2 as shown below is used instead of PEG-TML 3 acid (1).

Example 4b

The procedure of Example 4a is repeated except that Leucine-Doxorubicin is replaced by 20-S-alanine-camptothecin-TFA salt 6 (0.120 g, 0.196 mmol) to yield the final product.

Example 5a

In this example, the procedure of Example 1a is repeated except that compound 9, TML3β as shown below is used instead of PEG-TML3 acid (1).

Example 5b

The procedure of Example 5a is repeated except that Leucine-Doxorubicin is replaced by 20-S-alanine-camptothecin-TFA salt 6 (0.120 g, 0.196 mmol) to yield the final product.

Example 6a

In this example, the procedure of Example 1a is repeated except that compound 10, TML4 as shown below is used instead of TML3 (1).

Example 6b

The procedure of Example 6a is repeated except that Leucine-Doxorubicin is replaced by 20-S-alanine-camptothecin-TFA salt 6 (0.120 g, 0.196 mmol) to yield the final product.

Example 7a

In this example, the procedure of Example 1a is repeated except that compound 11, TML5 as shown below

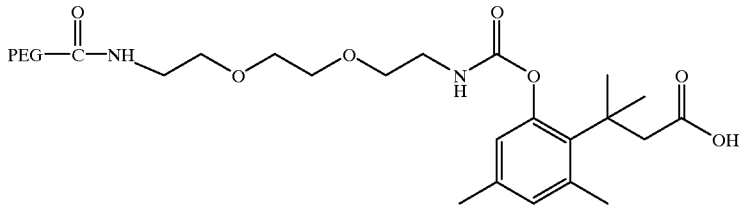

is used instead of PEG-TML3 acid (1).

Example 7b

The procedure of Example 7a is repeated except that Leucine-Doxorubicin is replaced by 20-S-alanine-camptothecin-TFA salt 6 (0.120 g, 0.196 mmol) to yield the final product.

Example 8

Conformation of Efficacy of Tetrapartate Prodrug Relative to Doxorubicin

Following at least one week of acclimation, tumors were established by injecting $1 \times 10^6$ (100 µl) harvested MX-1 mammary tumor cells in a single subcutaneous site, on the left axillary flank region of nude mice. The tumor injection site was observed twice weekly and measured once palpable. The tumor volume for each mouse was determined by measuring two dimensions with calipers and calculated using the formula: tumor volume ((length×width$^2$)/2). When tumors reached the average volume of approximately 65 mm$^3$, the mice were divided into their experimental groups, which consists of vehicles (20 m M Sodium PO$_4$ in 0.6% NaCl) controls, Leu-Doxorubicin, compound 3 of Example 1a, compound 5 of Example 2a. The mice were sorted to evenly distribute tumor size, grouped into 6 mice/cage, and ear punched for permanent identification. Drugs were dosed intravenously via the tail vein once per week for three weeks (Qd7×3). Mouse weight and tumor sizes were measured at the beginning of study and twice weekly through week 5.

The overall growth of tumors was calculated as the mean tumor volume at one week following the end of the treatment. A percent treatment over control (T/C) value was also calculated when the control group's median tumor size reached approximately 800–1100 mm$^3$ and again at one week following treatment. The T/C value in percent is a non-quantitative indication of anti-tumor effectiveness.

Data is presented in Table 1, below.

TABLE 1

Efficacy Comparison of PEG-Leu-Doxorubicin Analogs Against s.c. Human Mammary Tumor$^a$ (MX-1) in Nude Mice

| Compound | Dose (mg/kg) q7d × 3, iv | Tumor Vol. Mean ± SEM (Day 25–28) | % Change Mean ± SEM (Day 25–28) | T/C (%)$^\beta$ 1000 mm$^3$ |
|---|---|---|---|---|
|  |  | 3431 ± 291 | 6603 ± 1200 | — |
| Leu-Dox | 30 | 860 ± 163 | 1373 ± 487 | 56.5 |
| Compound 3 | 30 | 3227 ± 1003 | 3890 ± 1046 | 93.8 |
| Compound 5 | 30 | 1217 ± 351 | 2194 ± 684 | 54.2 |

$^a$Mean baseline tumor volume was 65 mm$^3$.
$^\beta$The median tumor volume of treatment and control groups were measured and compared when the control group's median tumor volume reached approximately 1000 mm$^3$. T/C < 42% at 1000 mm$^3$ is considered significant anti-tumor activity by the Drug Evaluation Branch of the NCI.

Thus, as can be appreciated from the data presented by Table 1, above, the PEG conjugate forms of leu-doxorubicin were about as effective than the non-conjugated parent compound. Furthermore, it is shown that attachment of the polymer did not significantly effect the efficacy of the parent compound.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

We claim:

1. A compound of Formula I:

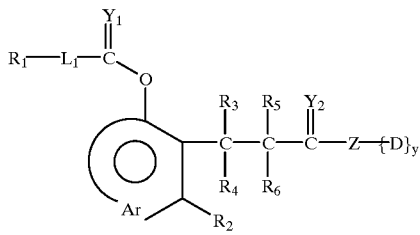

(I)

wherein:
$R_1$ is a mono- or bivalent polymer residue,
$L_1$ is a bifunctional linking group;
$Y_1$ and $Y_2$ are independently O, S or $NR_7$;
$R_{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
D is a moiety that is a leaving group or a residue of a compound to be delivered into a cell;
Z is selected from the group consisting of:
a moiety that is actively transported into a target cell, a hydrophobic moiety, and combinations thereof;
Ar is a moiety which when included in Formula (I) forms a multi-substituted aromatic hydrocarbon or a multi-substituted heterocyclic group; and
(y) is a positive integer greater than or equal to 1.

2. The compound of claim 1, wherein y is 1 or 2.

3. The compound of claim 1 wherein when y is 2, each of the two D moieties is the same or different.

4. The compound of claim 1 wherein Z is selected from the group consisting of an amino acid residue, a sugar residue, a fatty acid residue, a peptide residue, a $C_{6-18}$ alkyl, a substituted aryl, a heteroaryl, —C(=O), —C(=S), and —C(=$NR_{12}$), wherein $R_{12}$ is selected from the same group as $R_2$.

5. The compound of claim 4 wherein the amino acid residue is selected from the group consisting of alanine, valine, leucine, isoleucine, glycine, serine, threonine, methionine, cysteine, phenylalanine, tyrosine, tryptophan, aspartic acid, glutamic acid, lysine, arginine, histidine and proline.

6. The compound of claim 4 wherein the peptide residue ranges in size from 2 to about 10 amino acid residues.

7. The compound of claim 6 wherein the peptide residue is Gly-Phe-Leu-Gly (SEQ. ID NO:1) or Gly-Phe-Leu.

8. The compound of claim 1 wherein each D moiety is independently a residue of an active biological material.

9. The compound of claim 1 wherein each D moiety is independently a residue of an anticancer agent, an anticancer prodrug, a detectable tag, and combinations thereof.

10. The compound of claim 9 wherein the anticancer agent or anticancer prodrug comprises an anthracycline compound or a topoisomerase I inhibitor.

11. The compound of claim 9 wherein the anticancer agent or anticancer prodrug is selected from the group consisting of daunorubicin, doxorubicin, p-aminoaniline mustard, melphalan, cytosine arabinoside, gemcitabine, and combinations thereof.

12. The compound of claim 1 wherein at least one D moiety is a leaving group selected from the group consisting of as N-hydroxybenzotriazolyl, halogen, N-hydroxyphthalimidyl, p-nitrophenoxy, imidazolyl, N-hydroxysuccinimidyl, thiazolidinyl thione, and combinations thereof.

13. The compound of claim 1, wherein $Y_1$ and $Y_2$ are both O.

14. The compound of claim 1, wherein $R_1$ comprises a polyalkylene oxide residue.

15. The compound of claim 14, wherein said polyalkylene oxide residue comprises polyethylene glycol.

16. The compound of claim 1 wherein said polymer residue has a number average molecular weight of from about 2,000 to about 100,000 daltons.

17. The compound of claim 1, wherein said polymer residue has a number average molecular weight of from about 20,000 to about 40,000 daltons.

18. A compound of Formula (I):

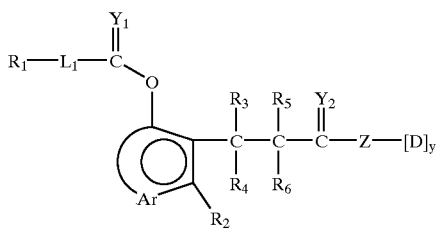

wherein:
$R_1$ is a mono- or bivalent polymer residue,
$L_1$ is a bifunctional linking group;
$Y_1$ and $Y_2$ are independently O, S or $NR_7$;
$R_{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;
D is a moiety that is a leaving group or a residue of a compound to be delivered into a cell;
Z is selected from the group consisting of:
a moiety that is actively transported into a target cell, a hydrophobic moiety, and combinations thereof;

Ar is selected from the group consisting of

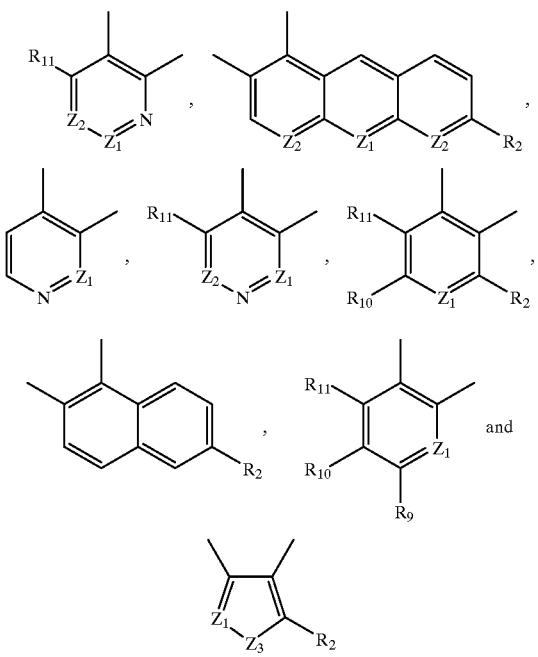

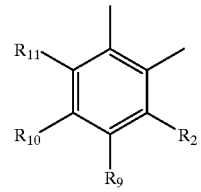

wherein
$R_2$, $R_9$, $R_{10}$ and $R_{11}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$Z_1$ and $Z_2$ are independently $CR_{23}$ or $NR_{24}$; and $Z_3$ is O, S or $NR_{25}$ where $R_{23-25}$ are selected from the same group as that which defines $R_2$ or a cyano, intro, carboxyl, acyl, substituted acyl or carboxyalkyl;

and (y) is a positive integer greater than or equal to 1.

19. The compound of claim 1, wherein Ar is

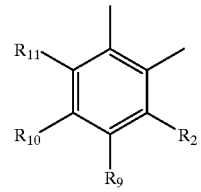

wherein
$R_2$, $R_9$, $R_{10}$ and $R_{11}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy.

20. The compound of claim 19 wherein $R_2$ is $CH_3$.

21. The compound of claim 1 that is selected from the group consisting of

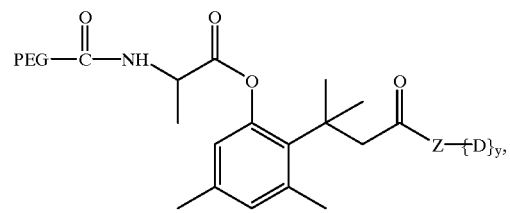

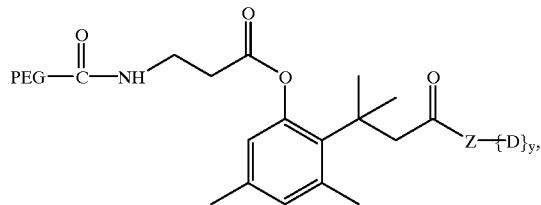

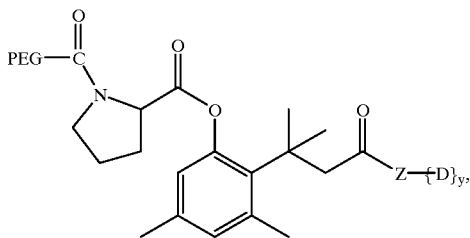

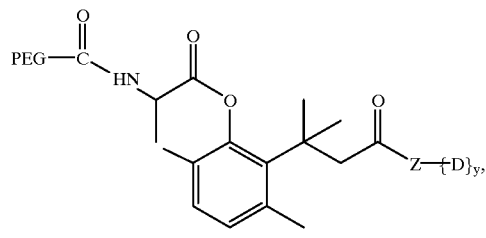

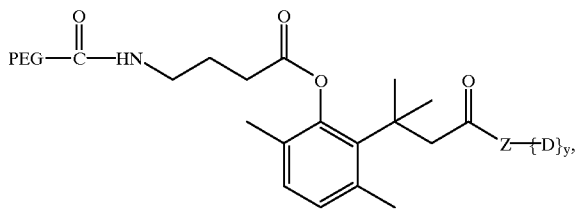

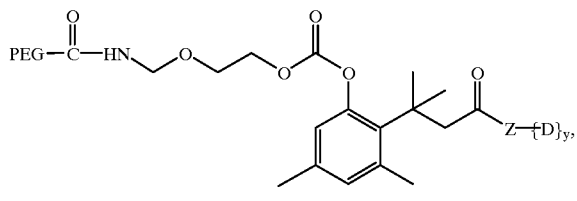

and

-continued

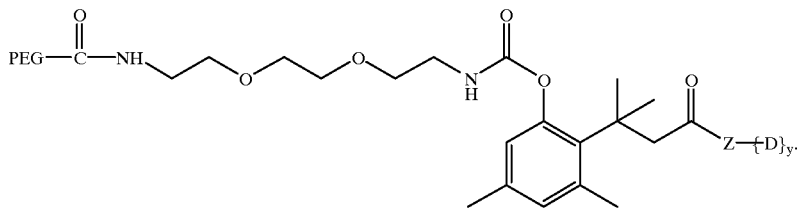

22. A compound of claim 21 wherein each polyethylene glycol (PEG) residue has a number average molecular weight of from about 20,000 to 40,000 daltons.

23. A composition comprising a pharmaceutically or diagnostically effective amount of the compound of claim 1, where D is a residue of a compound to be delivered into the cell, together with a carrier acceptable for in vivo administration to an animal in need thereof.

24. A method of preparing a tetrapartate prodrug comprising reacting a compound of formula:

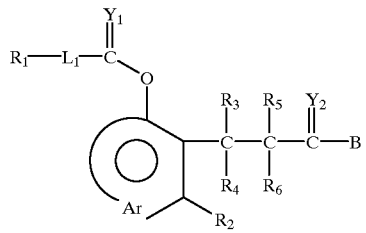

(II)

with a compound of formula:

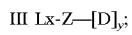

III Lx-Z—[D]$_y$;

wherein

B is a leaving group for Formula II;

Lx is a leaving group for Formula III;

Z is covalently linked to [D]$_y$, wherein Z is selected from the group consisting of: a moiety that is actively transported into a target cell, a hydrophobic moiety, and combinations thereof;

$R_1$ is a polymeric residue;

$L_1$ is a bifunctional linking group;

$Y_1$ and $Y_2$ are independently O, S or $NR_7$;

$R_{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

D is a moiety that is a leaving group or a residue of a compound to be delivered into a cell;

Ar is a moiety which when included in Formula (I) forms a multi-substituted aromatic hydrocarbon or a multi-substituted heterocyclic group; and (y) is 1 or 2.

25. A method of preparing a tetrapartate prodrug comprising reacting a compound of formula

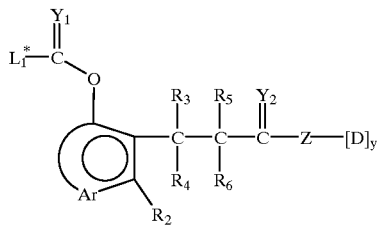

(IV)

with at least one biologically active material; wherein $R_1$ is a polymeric residue;

$L_1$ is a bifunctional linking group;

$Y_1$ and $Y_2$ are independently O, S or $NR_7$;

$R_{2-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

Z is covalently linked to La and wherein Z is selected from the group consisting of: a moiety that is actively transported into a target cell, a hydrophobic moiety and combinations thereof;

Ar is a moiety which when included in Formula (I) forms a multi-substituted aromatic hydrocarbon or a multi-substituted heterocyclic group; and La is a leaving group for Formula IV wherein Z is covalently linked thereto.

26. A method of treating a disease or disorder in an animal, that comprises administering a pharmaceutically acceptable composition comprising an effective amount of a compound of claim 1, where D is a moiety that is a residue of a compound to be delivered into a cell; to an animal in need thereof.

27. A method of delivering a biologically active material D into a cell in need of treatment therewith, comprising the process of administering a compound of claim 1 to an animal comprising said cell, wherein Formula I is hydrolyzed in vivo extracellularly to yield:

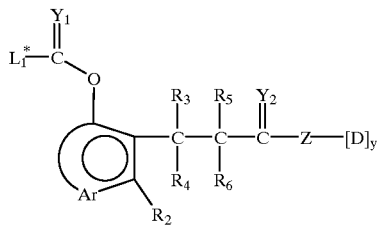

wherein $L_1^*$ is the remainder of $L_1$, after hydrolysis of the polymeric residue ($R_1$); and Formula (I-i) subsequently spontaneously hydrolyzes to Formula (I-ii)

(I-ii)
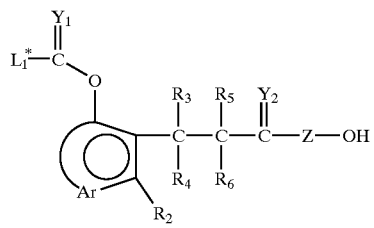
and Formula I-(iii) Z—[D]y;
and Z—[D]$_y$ crosses the membrane of the cell, and is hydrolyzed therein to release D.
* * * * *